US010588644B2

(12) United States Patent
Karg et al.

(10) Patent No.: US 10,588,644 B2
(45) Date of Patent: Mar. 17, 2020

(54) GUIDE ATTACHMENT FOR POWER TOOLS

(71) Applicant: DEPUY SYNTHES PRODUCTS, INC., Raynham, MA (US)

(72) Inventors: Nicholas Karg, Solothurn (CH); Nils Schmuckli, Sissach (CH); Andre Furrer, Lüterkofen (CH); Mike Santini, West Chester, PA (US); Samantha Weber, Bridgewater, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 188 days.

(21) Appl. No.: 15/691,906

(22) Filed: Aug. 31, 2017

(65) Prior Publication Data
US 2019/0059915 A1 Feb. 28, 2019

(51) Int. Cl.
*A61B 17/16* (2006.01)
(52) U.S. Cl.
CPC .................. *A61B 17/164* (2013.01)
(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1631; A61B 17/1633; A61B 17/164; A61B 17/1655; A61B 17/1657
See application file for complete search history.

(56) References Cited

U.S. PATENT DOCUMENTS

| 4,722,336 | A | | 2/1988 | Kim et al. |
| 5,569,255 | A | | 10/1996 | Burke |
| 5,584,838 | A | * | 12/1996 | Rona ................... A61B 17/1707 324/226 |
| 7,873,400 | B2 | | 1/2011 | Moctezuma DeLaBarrera et al. |
| 8,366,719 | B2 | * | 2/2013 | Markey ............. A61B 17/1626 606/104 |
| 8,689,801 | B2 | * | 4/2014 | Ritchey ............. A61B 17/1707 128/899 |
| 8,757,875 | B2 | | 6/2014 | Mayer |
| 9,192,400 | B2 | | 11/2015 | Patwardhan |

(Continued)

OTHER PUBLICATIONS

International Search Report and Written Opinion (PCT/IB2018/056332) dated Feb. 11, 2019, 7 pages.

(Continued)

*Primary Examiner* — Eric S Gibson
(74) *Attorney, Agent, or Firm* — Wayne C. Jaeschke, Jr.

(57) ABSTRACT

A distal targeting device for a surgical instrument includes a field generator having a coupling element configured to receive a shaft that is elongate along an axis and a bridge connectable to the field generator so as to be spaced from the field generator in a proximal direction with respect to the axis. The bridge includes an attachment device that is connectable to a tool that is configured to manipulate the shaft. The bridge also includes a pair of arms configured to clasp a body of the tool in a manner substantially rigidly coupling the bridge to the tool. At least one of the arms is positionable with respect to the attachment member at a distance that is adjustable so as to enable the arms to substantially rigidly clasp tool bodies having one or more of various shapes and sizes.

22 Claims, 25 Drawing Sheets

(56) References Cited

U.S. PATENT DOCUMENTS

| | | | |
|---|---|---|---|
| 9,216,048 B2* | 12/2015 | Markey | A61B 17/1626 |
| 9,451,999 B2 | 9/2016 | Simpson et al. | |
| 9,554,812 B2* | 1/2017 | Inkpen | G01B 7/003 |
| 9,687,306 B2* | 6/2017 | Markey | A61B 17/1626 |
| 2004/0011365 A1* | 1/2004 | Govari | A61B 17/1707 |
| | | | 128/899 |
| 2004/0106916 A1* | 6/2004 | Quaid | G06F 3/0346 |
| | | | 606/1 |
| 2004/0167391 A1* | 8/2004 | Solar | A61B 90/39 |
| | | | 600/411 |
| 2005/0070916 A1* | 3/2005 | Hollstien | A61B 17/1707 |
| | | | 606/96 |
| 2005/0267354 A1* | 12/2005 | Marquart | A61B 90/36 |
| | | | 600/411 |
| 2006/0241628 A1* | 10/2006 | Parak | A61B 17/1626 |
| | | | 606/80 |
| 2007/0016009 A1* | 1/2007 | Lakin | A61B 90/39 |
| | | | 600/424 |
| 2008/0183189 A1* | 7/2008 | Teichman | A61B 17/1655 |
| | | | 606/130 |
| 2008/0183190 A1* | 7/2008 | Adcox | A61B 17/1655 |
| | | | 606/130 |
| 2010/0106194 A1* | 4/2010 | Bonutti | A61B 17/0218 |
| | | | 606/279 |
| 2010/0241129 A1* | 9/2010 | Markey | A61B 17/1626 |
| | | | 606/104 |
| 2012/0226094 A1* | 9/2012 | Ritchey | A61B 17/1707 |
| | | | 600/12 |
| 2013/0085505 A1* | 4/2013 | Markey | A61B 17/1626 |
| | | | 606/104 |
| 2013/0218007 A1 | 8/2013 | Petteys et al. | |
| 2014/0148808 A1* | 5/2014 | Inkpen | G01B 7/003 |
| | | | 606/80 |
| 2015/0223897 A1* | 8/2015 | Kostrzewski | A61B 17/1615 |
| | | | 606/130 |
| 2016/0166337 A1* | 6/2016 | Markey | A61B 17/1626 |
| | | | 606/97 |
| 2017/0164958 A1 | 6/2017 | Rich | |
| 2017/0304011 A1* | 10/2017 | Markey | A61B 17/1626 |
| 2018/0199951 A1* | 7/2018 | Chappuis | A61B 17/1615 |
| 2018/0200002 A1* | 7/2018 | Kostrzewski | A61B 34/25 |
| 2018/0200016 A1* | 7/2018 | Chappuis | A61B 34/70 |
| 2018/0289432 A1* | 10/2018 | Kostrzewski | A61B 34/20 |
| 2019/0059915 A1* | 2/2019 | Karg | A61B 17/1707 |

OTHER PUBLICATIONS

Written Opinion (PCT/IB2018/056332) dated Feb. 11, 2019, 10 pages.

* cited by examiner

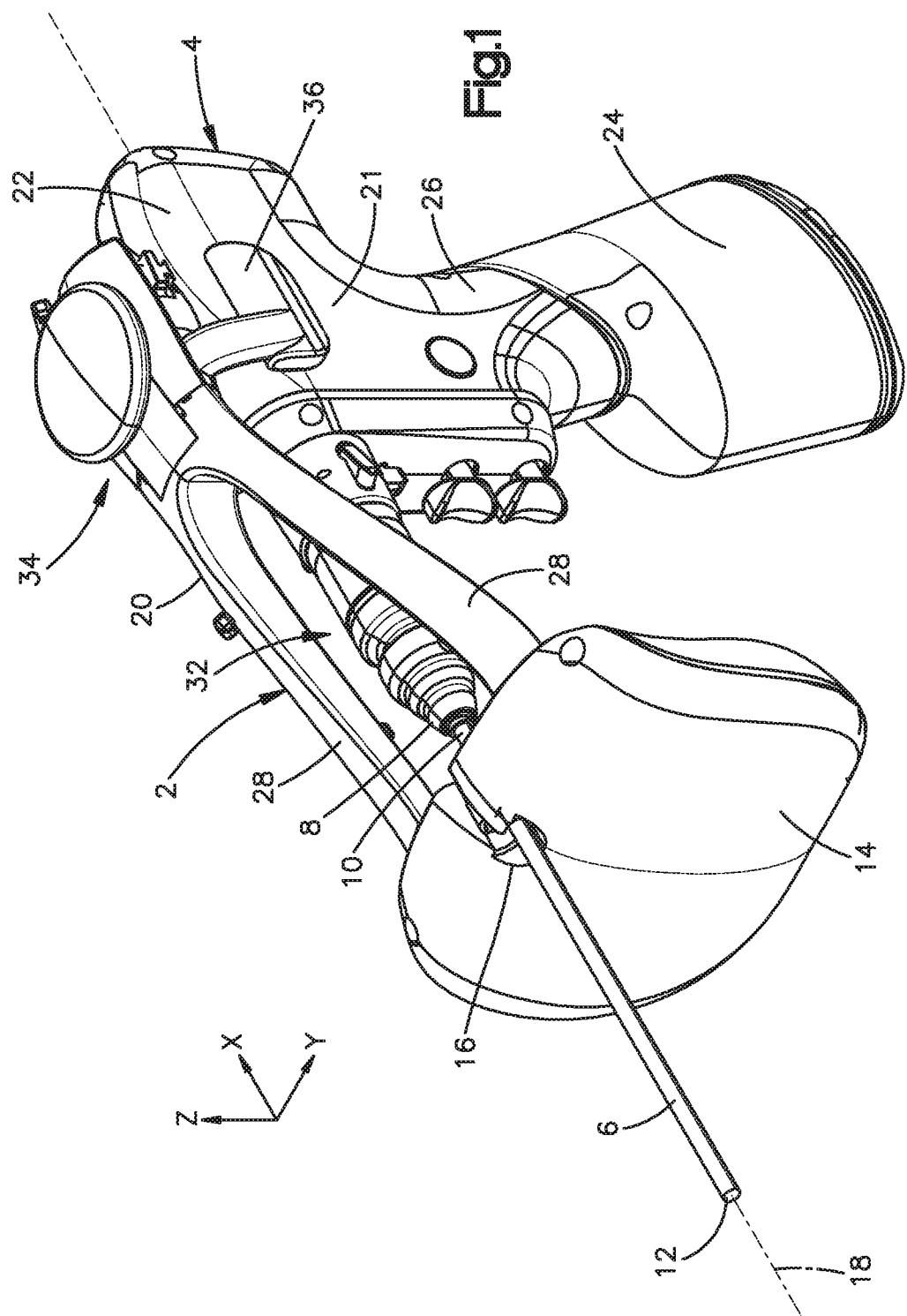

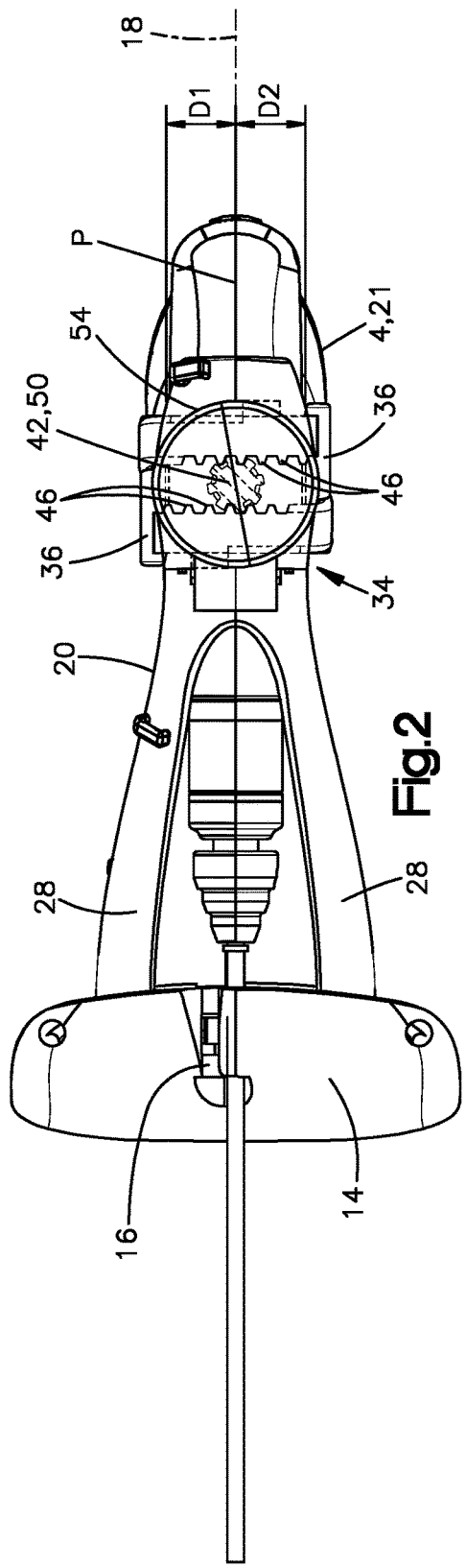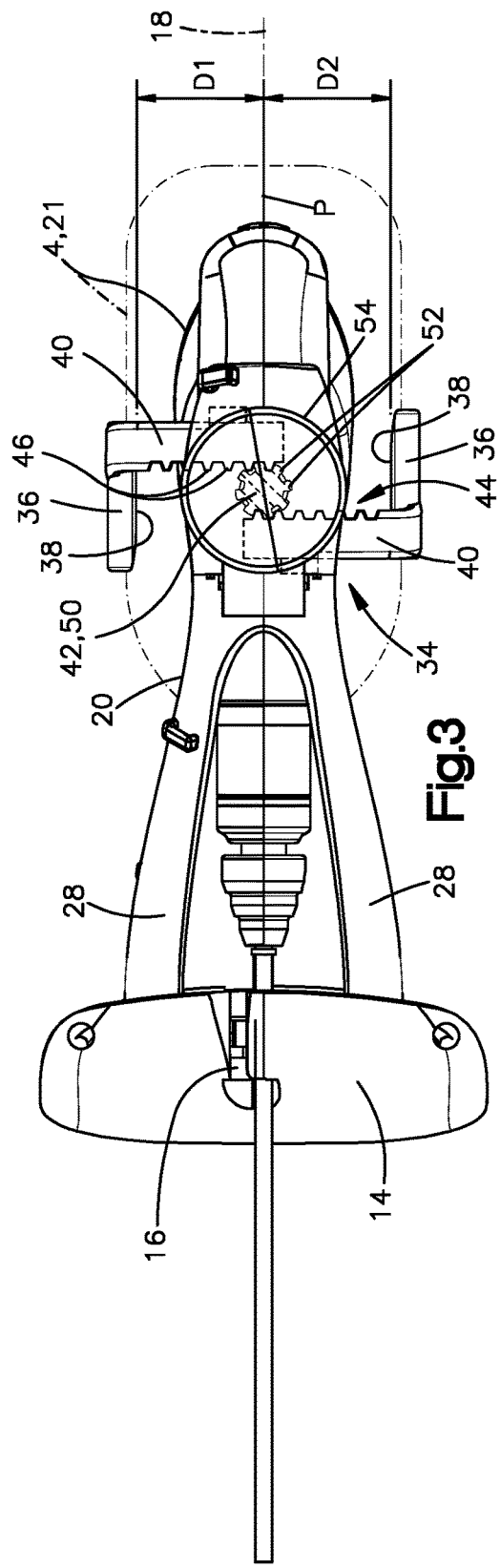

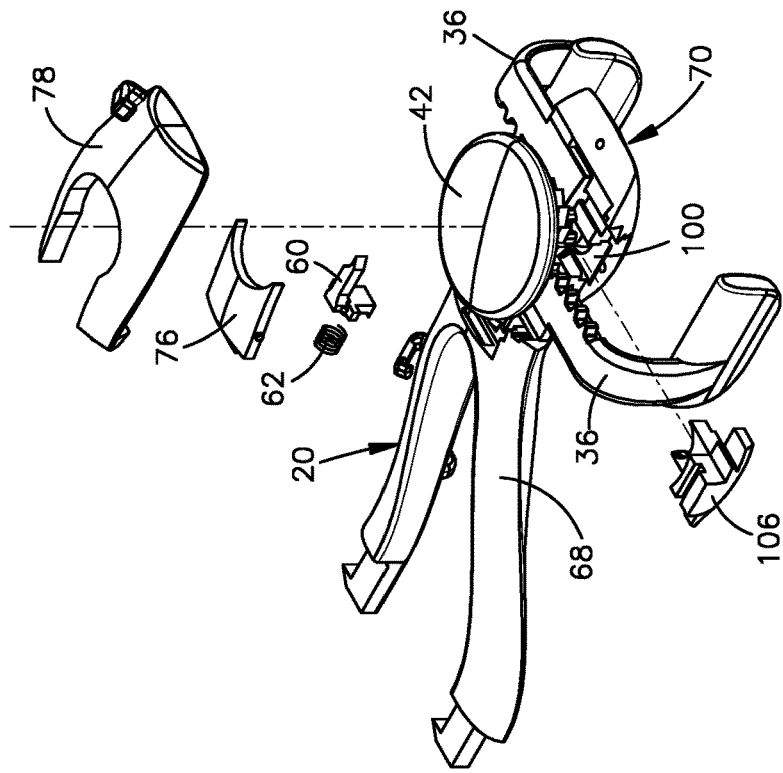
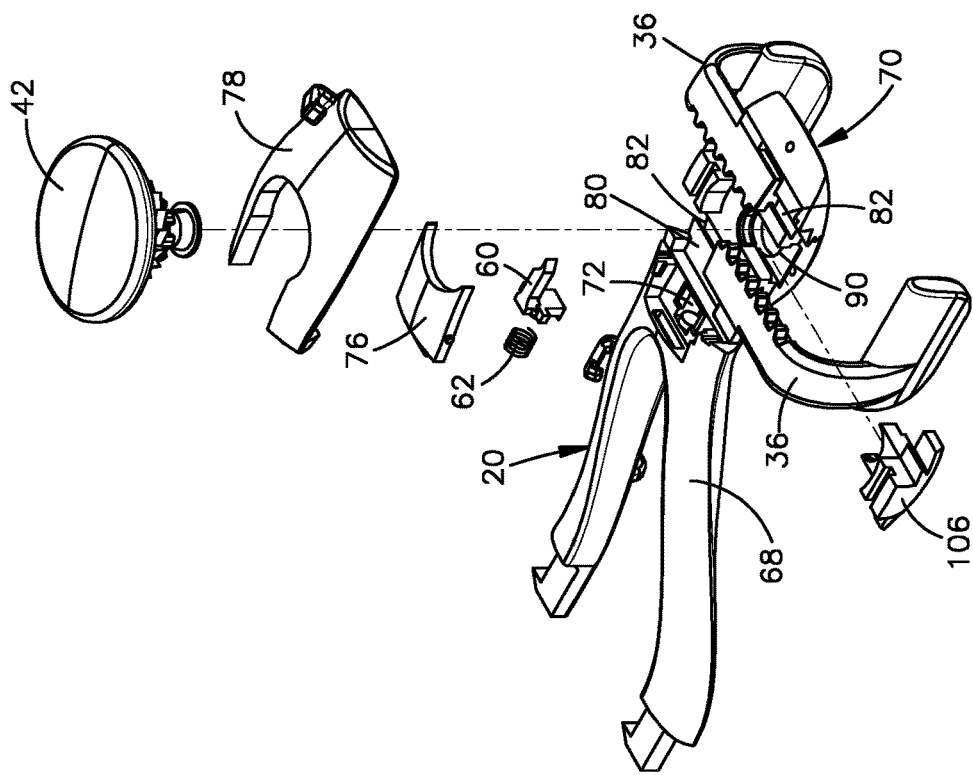

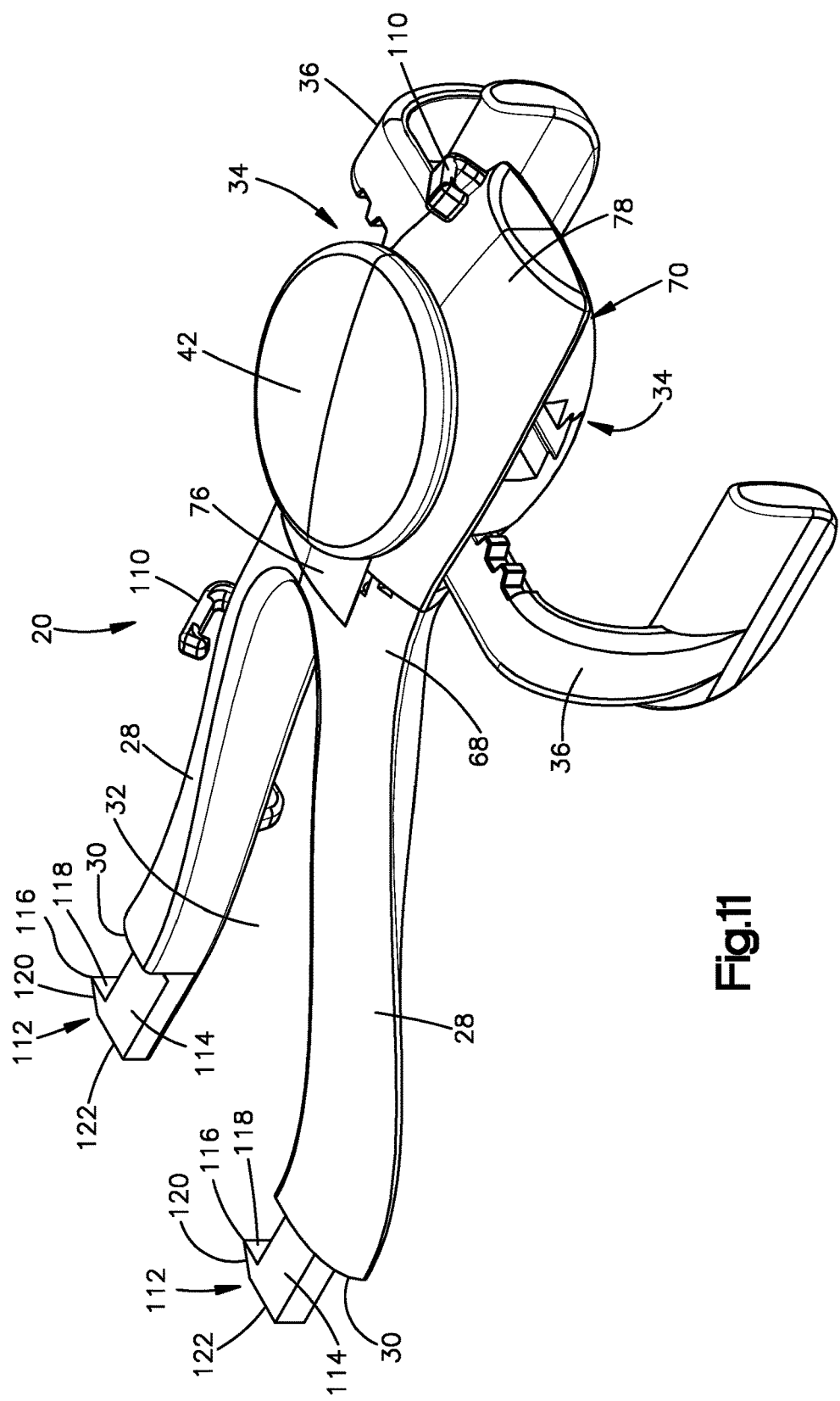

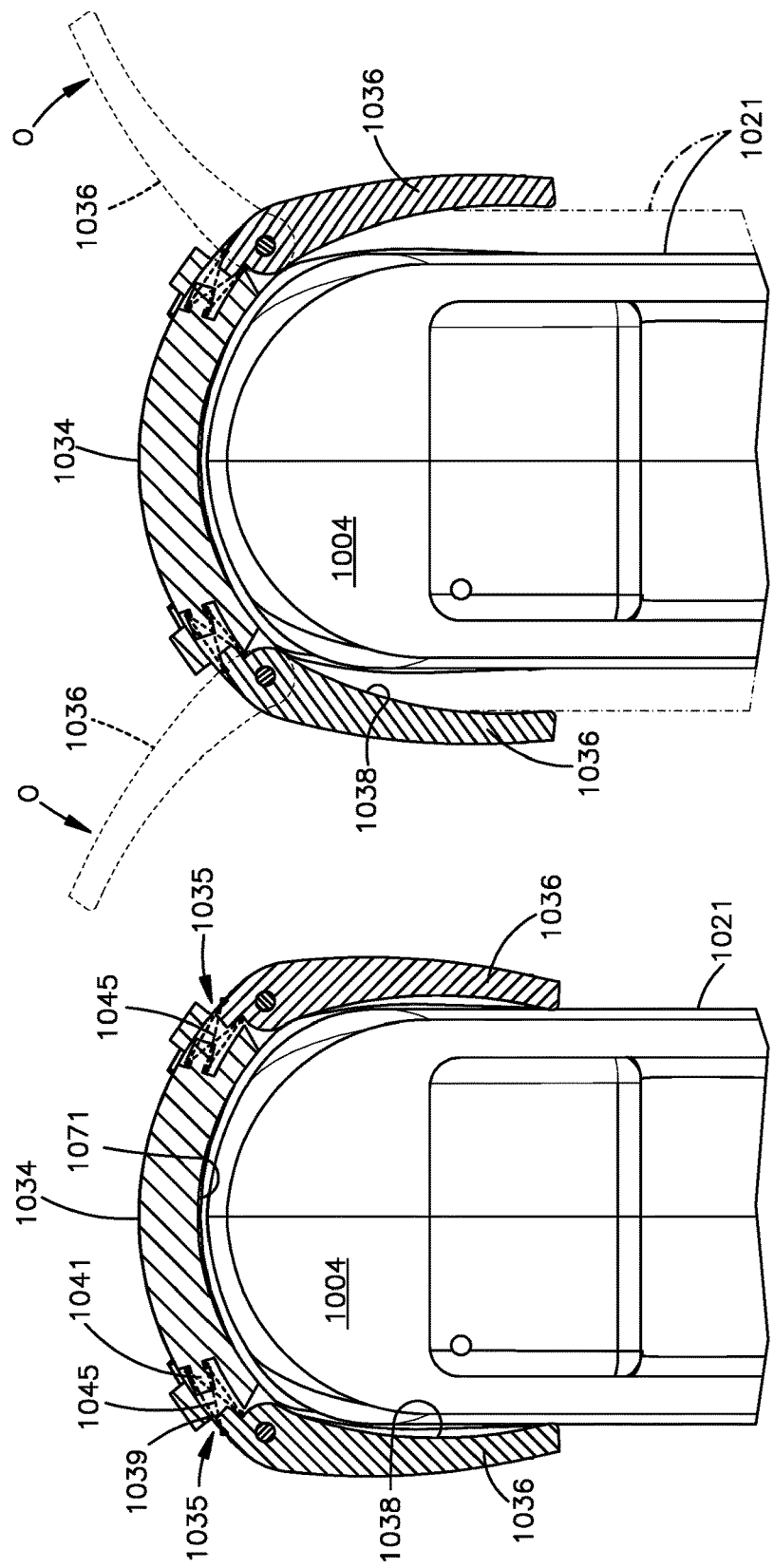

GUIDE ATTACHMENT FOR POWER TOOLS

TECHNICAL FIELD

The present disclosure relates to distal targeting devices for use with surgical implants, and more particularly to distal targeting devices having an adjustable attachment device for attaching the distal targeting device to power tools of various sizes and/or shapes.

BACKGROUND

Surgical implants can include mechanisms that require external manipulation during or after implantation. For example, an implant can include anchoring elements, locking elements, position-adjusting elements, or other types of elements or features that allow the implant to operate in a manner to promote healing and/or stabilization of the anatomy of the patient. One example of such an implant includes an intramedullary nail implanted within a medullary cavity of a long bone, such as a femur, for example, to stabilize a fracture in the bone. It has been common practice to affix the intramedullary nail with respect to the bone by placing locking members, such as screws, through access holes drilled through at least a cortex of the bone and in alignment with anchoring holes, such as threaded bores, that are pre-drilled transversely in the nail. The procedure presents technical difficulties, as the pre-drilled bores in the intramedullary nail are not generally visible to the surgeon, and are difficult to localize and to align with surgical drills and placement instruments for drilling the access holes in the bone and/or inserting the locking members.

Distal targeting systems are used in many instances to detect the location of various elements of an implant during a surgical procedure. With respect to the foregoing intramedullary nail example, a distal targeting system can be employed with the surgical drill to locate the position of the one or more anchoring bores in the intramedullary nail and provide feedback to the physician indicating the relative positions of the anchoring bores with respect to a distal end of a drill bit of the surgical drill. Such distal targeting systems can include a magnetic field generator (also referred to as simply a "field generator") having a central guide bore in which the drill bit is received. The field generator includes circuitry for generating one or more magnetic fields. The intramedullary nail can include one or more sensors each having one or more field transponders configured to detect the direction and strength of the magnetic fields generated by the field generator. The one or more sensors can each transmit magnetic field data to a control unit having control circuitry. The one or more sensors can be located with respect to the intramedullary nail so that the relative positions of the one or more sensors and the one or more anchoring bores are known by the control unit. The orientation and position of a central axis of the guide bore are also known by the control unit. The central axis of the guide bore approximates a central axis of a drill bit received within the guide bore.

The control unit interprets the data from the one or more sensors to ascertain the orientation and displacement of the central axis of the guide bore relative to the one or more anchoring bores in the intramedullary nail. The control unit transmits feedback to the physician, such as visual feedback via a view screen or audio feedback via a speaker, indicating the orientation and/or displacement of the central axis in relation to the anchoring bores in the intramedullary nail. Distal targeting systems for use with other types of surgical implants can employ similar structures and techniques.

SUMMARY

In one embodiment of the present disclosure, a distal targeting device for a surgical instrument includes a field generator having a coupling element configured to receive a shaft that is elongate along an axis and a bridge connectable to the field generator so as to be spaced from the field generator in a proximal direction with respect to the axis. The bridge includes an attachment device that is connectable to a tool that is configured to manipulate the shaft. The bridge also includes a pair of arms configured to clasp a body of the tool in a manner substantially rigidly coupling the bridge to the tool. At least one of the arms is positionable with respect to the attachment member at a distance that is adjustable so as to enable the arms to substantially rigidly clasp tool bodies having one or more of various shapes and sizes.

In another embodiment of the present disclosure, a field generator that is configured to align a shaft of a surgical instrument with a target includes a housing containing field generator circuitry and a coupling element at least partially defining an opening that has an opening proximal end and an opening distal end spaced from one another along a longitudinal direction. The opening is open in a transverse direction that is substantially perpendicular to the longitudinal direction so as to receive the shaft without a distal end or a proximal end of the shaft passing through the opening.

In an additional embodiment of the present disclosure, a distal targeting system includes a power tool having a tool body and a receiving element. The system includes a shaft elongated along an axis extending along a longitudinal direction. A proximal portion of the shaft is receivable in the receiving element of the power tool. The system includes a field generator having a coupling element configured to receive the shaft. The system also includes a bridge connectable to the field generator so as to be spaced from the field generator in a proximal direction with respect to the axis. The bridge includes an attachment device that is connectable to the driving tool and a pair of arms configured to clasp the tool body in a manner substantially rigidly coupling the bridge to the tool. At least one of the arms is positionable with respect to the attachment device at a distance that is adjustable so as to enable the arms to 1) substantially rigidly clasp the tool body, 2) release the tool body, and 3) substantially rigidly clasp a second tool body having one or more of a different size and shape than the tool body.

BRIEF DESCRIPTION OF THE DRAWINGS

The foregoing summary, as well as the following detailed description of illustrative embodiments of the distal targeting device of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 1 is a perspective view of a distal targeting device coupled to a power tool so as to comprise a distal targeting system, according to an embodiment of the present disclosure;

FIG. 2 is a top view of the distal targeting device of FIG. 1;

FIG. 3 is a top view of the distal targeting device of FIG. 1 with clamp arms of the device in an extended position;

FIG. 7 is a partial exploded view of the bridge of FIG. 5, wherein a first step of assembling the attachment device is shown according to one example assembly sequence;

FIG. 8 is a partial exploded view of the bridge of FIG. 5, wherein a second step of assembling the attachment device is shown according to the example assembly sequence;

FIG. 11 is a perspective view of the bridge of FIG. 5, wherein a fifth step of assembling the attachment device is shown according to the example assembly sequence;

FIG. 28 is a sectional end view of the distal targeting device of FIG. 27, showing clamp arms of the device in a closed position;

FIG. 29 is a sectional end view of the distal targeting device of FIG. 27, showing the clamp arms in another position, as well as in an optional fully open position in phantom lines;

DETAILED DESCRIPTION OF ILLUSTRATIVE EMBODIMENTS

Figure 4:
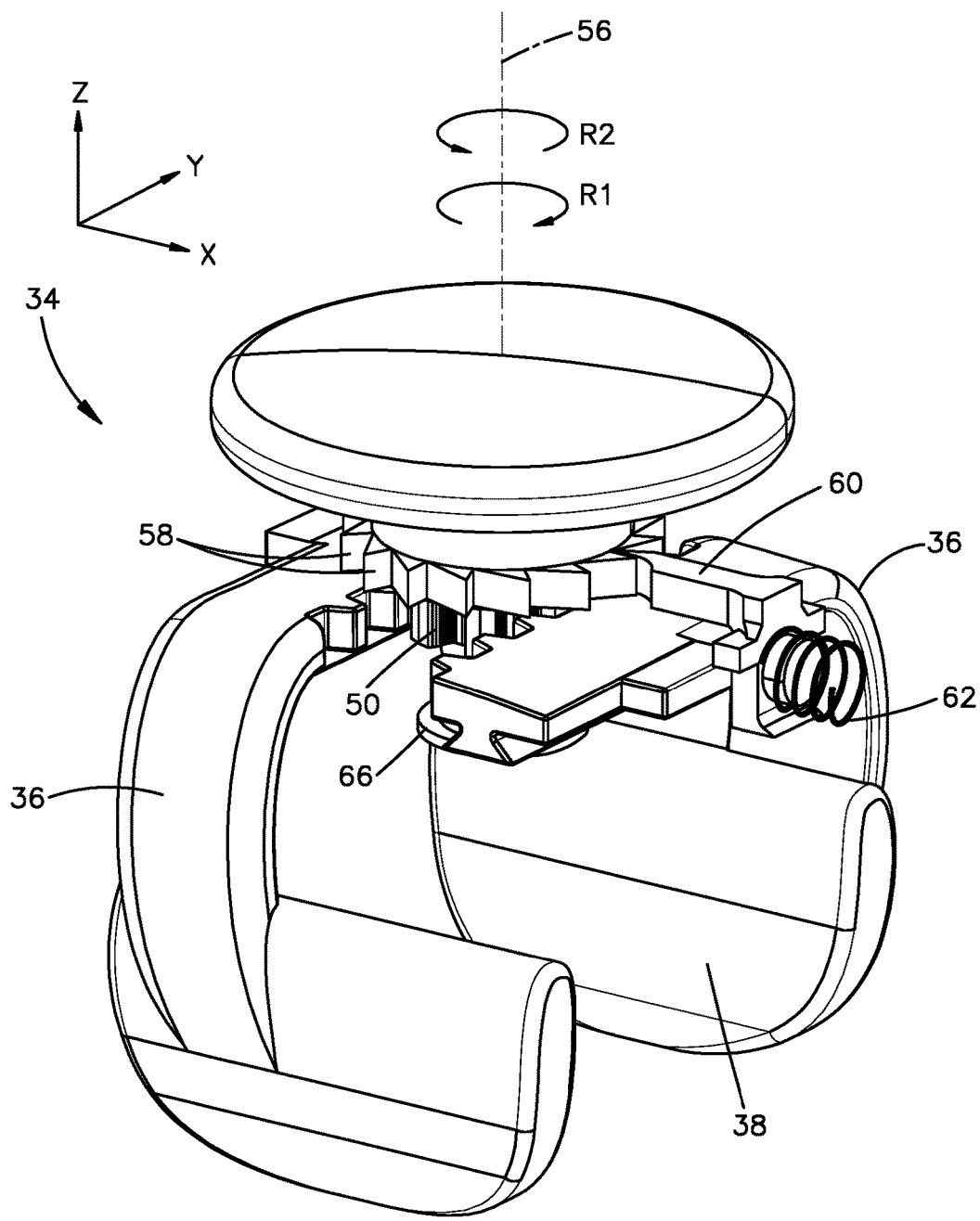
FIG. 4 is a perspective view of elements of an attachment device of the distal targeting device of FIG. 1.

In procedures involving distal targeting of an implant with a surgical instrument, it is advantageous to provide as exact a relationship as possible between the implant and the surgical instrument. The present disclosure relates to a distal targeting device that can be mounted on a surgical instrument, such as a power drill, to guide a physician attempting to align a distal portion of the surgical instrument, such as the distal end of a drill bit, with a portion of a surgical implant disposed in a patient. In particular, the distal targeting devices disclosed herein each have a mounting element that is adjustable in a manner allowing the targeting device to be readily mounted in sturdy, rigid fashion to surgical instruments of various sizes and/or shapes. This enables the distal targeting device and any one of numerous surgical instruments to be used as one distal targeting system by a single physician. By way of non-limiting example, the vast majority of power drills designed for drilling access holes in the cortex of a bone are commercially produced so that the width of the respective tool, such as at the motor cowling, is within a range of about 2.50 cm and about 5.12 cm. The mounting elements of the distal targeting devices disclosed herein are size-adjustable to couple to a power having a width in the foregoing range. Accordingly, the mounting elements for the distal targeting devices disclosed herein can be characterized as "universal mounting elements." The distal targeting devices disclosed herein provide significant commercial advantages, as the same targeting device can be employed on the vast majority of commercially available power drills within a surgical field, such as the field of intramedullary nail implantation.

The present disclosure also relates to a field generator of the distal targeting device. In particular, the field generators disclosed herein include a transverse-entry opening allowing a portion of the drill bit to be inserted transversely into the field generator, instead of requiring nearly the entire drill bit to be inserted axially, either distal-end-first or proximal-end-first, through the opening. Additionally, the field generators disclosed herein are connectable to the mounting elements of the distal targeting devices in a manner such that the field generator is supported by the mounting element while the drill bit extends through the opening of the field generator. In this manner, the field generator substantially does not exert a bending moment on the drill bit during operation. Thus, an assistant is not needed to manually steady the field generator while the physician operates the power drill.

Referring now to FIG. 1, an embodiment of a distal targeting system is shown that includes a distal targeting device 2 mounted to a tool 4 that is configured to receive and manipulate a shaft 6 for insertion within the body of a patient. As shown, the tool 4 can be a power tool, such as a hand-operated power drill, for rotating the shaft 6. The shaft 6 can be a bit, such as a drill bit, a driver bit, or any other type of shaft for targeted insertion within the patient. The power tool 4 can include a receiving element, such as a chuck 8, for receiving a proximal portion 10 of the shaft 6. The shaft 6 defines a distal end 12 spaced from the proximal portion 10 in a distal direction. The distal targeting device 2 can include a field generator 14 for generating a magnetic field as set forth above. The field generator 14 includes a coupling element 16 configured to receive a portion of the shaft 6. The shaft 6 defines a shaft axis 18 that extends along a longitudinal direction X.

The distal targeting device 2 includes a mounting element 20 that extends from the field generator 14 in a proximal direction opposite the distal direction. It is to be appreciated that the proximal and distal directions are each mono-directional components of the longitudinal direction X, which is bi-directional. The mounting element 20 is configured to mount the field generator 14 to a body 21 of the power tool 4. Thus, the mounting element 20 is also referred to herein as a "bridge." In the illustrated embodiments, the bridge 20 mounts to a top portion 22 of the tool body 21, such as at the motor cowling. However, in other embodiments, the bridge 20 can mount to another portion of the tool body 21, such as at a base 24 of the handle 26, for example. The bridge 20 is adjustable so that the field generator 14 can be mounted to power tools 4 of various sizes and/or various shapes.

The bridge 20 can also define a pair of distally extending branches 28 that extend outwardly with respect to a lateral direction Y that is substantially perpendicular to the longitudinal direction X. The longitudinal and lateral directions X, Y can each be termed a "horizontal" direction. Additionally, any plane coextensive with both of the longitudinal and lateral directions X, Y can be termed a horizontal plane. The longitudinal and lateral directions X, Y are each perpendicular to a vertical direction Z. As used herein, the term "longitudinally" means "along the longitudinal direction X"; the term "laterally" means "along the lateral direction Y"; and the term "vertically" means "along the vertical direction Z". As used herein, a "vertical-longitudinal plane" means a plane extending along the vertical and longitudinal directions Z, X; and a "vertical-lateral plane" means a plane extending along the vertical and lateral directions Z, Y.

Distal ends 30 of the branches 28 can couple to the field generator 14, as discussed in more detail below. The branches 28 can define a lateral space 32 therebetween, so that the shaft 6 can extend distally from the power tool 4, through the lateral space 32, and into the coupling element 16 of the field generator 14. The bridge 20 can include an attachment device 34 that is connectable to the tool body 21 and to a pair of clamp arms 36. The attachment device 34 can be configured to manipulate the arms 36 so as to clasp the tool body 21 in a manner substantially rigidly coupling the bridge 20 to the tool 4. In this manner, the attachment device 34 and the clamp arms 36 can cooperatively define a clamp.

As shown in FIGS. 2 and 3, the arms 36 can be configured to contact opposite sides of the tool body 21 so as to clamp or otherwise clasp the tool body 21 between the arms 36. One or both of the arms 36 can be positionally adjustable with respect to the attachment device 34 so as to clamp to power tools 4 of various sizes and/or shapes. For example, each arm 36 can define a respective arm distance D1, D2, measured along the lateral direction Y, from a central, vertical-longitudinal plane P (i.e., a plane that is coextensive with the shaft axis 18 and extends along a vertical direction Z) to an inner contact surface 38 of the arm 36. The vertical direction Z is substantially perpendicular to the longitudinal and lateral directions X, Y. The inner contact surfaces 38 of the arms 36 can define a curved, concave profile in a vertical-lateral plane. The foregoing profile can enhance the clamping grip of the arms 36 to the tool body 21, particularly if the tool body 21 has a rounded, convex profile in a vertical-lateral plane. The inner surfaces 38 of the arms 36 can also include a layer of high-friction material for increasing clamping grip of the arms 36 to the tool body 21.

With continued reference to FIGS. 2 and 3, both of the arms 36 can be manipulated by the attachment device 34 to adjust the respective arm distances D1, D2 to clamp to the power tool 4 as needed. In the illustrated embodiments, the arm distances D1, D2 can each be adjusted between a minimum (FIG. 2) of about 1.00 cm and a maximum (FIG. 3) of about 3.50 cm. As set forth above, this range of arm distances D1, D2 is sufficient to allow the bridge 20 to be mounted to the vast majority of power tools 4 for use with an intramedullary nail, including power tools 4 having various shapes and/or sizes. In other embodiments, one of the arms 36 can be static while the other is adjustable to clamp to the power tool 4. The arms 36 and the attachment device 34 can collectively define a rack and pinion mechanism to adjusting the arm distances D1, D2. In particular, the arms 36 can each define an adjustment portion 40 elongated along the lateral direction Y and configured to engage an actuator 42 of the attachment device 34. The adjustment portion 40 of each arm 36 can define a rack 44 having linearly aligned rack teeth 46. The actuator 42 can include an actuation shaft 48 (shown in FIG. 5) carrying a pinion 50 having radial pinion teeth 52 configured to intermesh with the rack teeth 46. The actuator 42 can include a knob 54 coupled to the pinion 50. The knob 54 can allow manual rotation of the pinion 50 about a central axis 56 (FIG. 5) of the actuation shaft 48 so as to translate the clamp arms 36 to adjust the arm distances D1, D2.

Referring now to FIG. 4, the attachment device 34 can include an arm expansion inhibitor, such as a ratchet, configured to prevent the arms 36 from moving laterally outward after the arms 36 are clamped onto the tool body 21. The ratchet can include ratchet teeth 58 circumferentially spaced around the actuation shaft 48. The ratchet teeth 58 can be positioned vertically between the pinion 50 and the knob 54. The ratchet can include a pawl 60 configured to engage the ratchet teeth 58 and a pawl spring 62 coupled to the pawl 60. The pawl 60 can be configured to engage the ratchet teeth 58 so as to allow the pinion 50 to rotate in a first rotational direction R1 so as to decrease the arm distances D1, D2 while impeding rotation of the pinion 50 about a second rotational direction R2 opposite the first rotational direction R1. While only one pawl 60 is present in the illustrated embodiment, it is to be appreciated that additional pawls 60 can be employed to engage the ratchet teeth 58. The actuator 42 can include a stem 64 extending below the pinion 50. The actuator 42 can also include a flange 66 at the bottom end of the stem 64.

Figure 5:
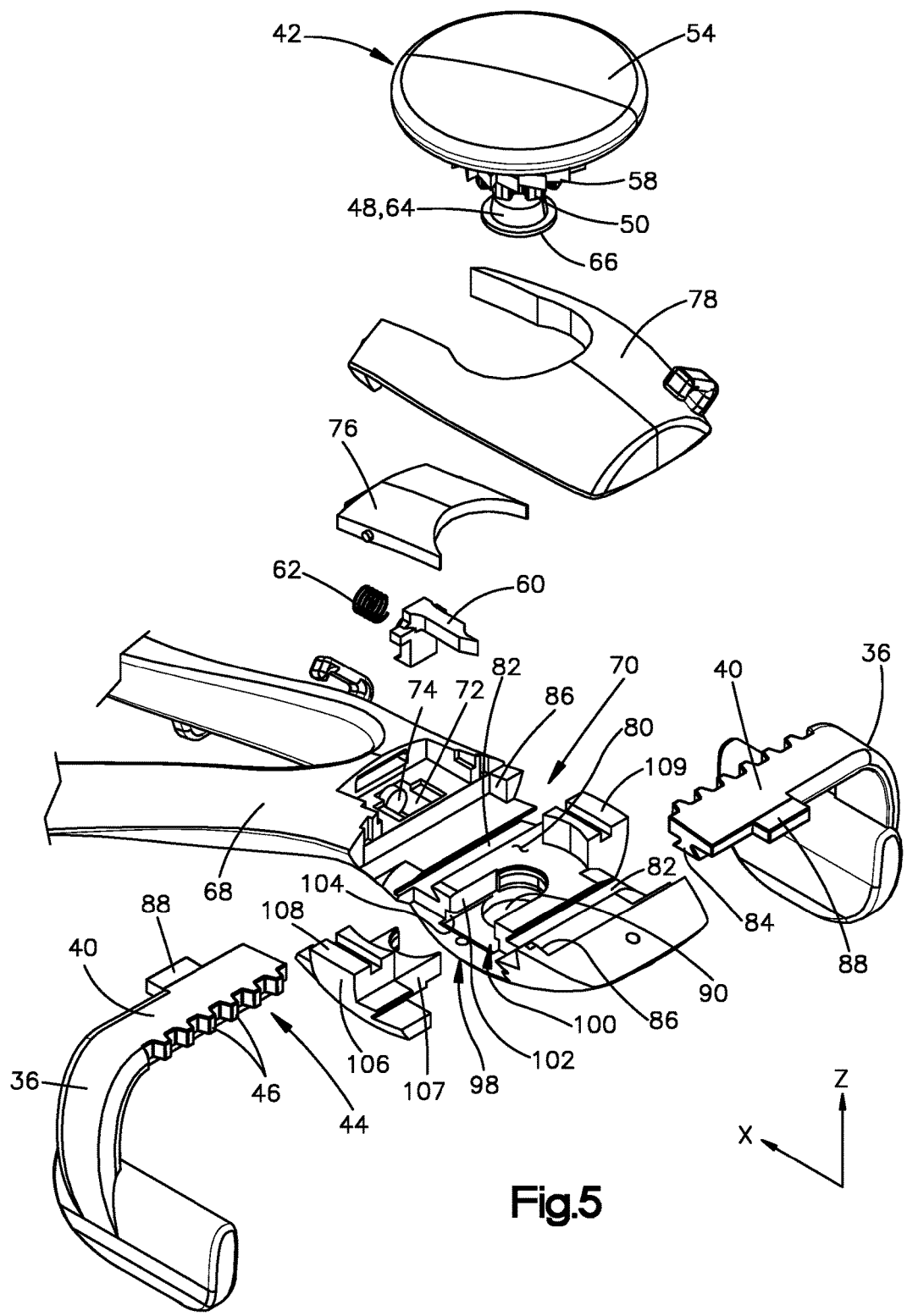
FIG. 5 is an exploded view of a bridge of the distal targeting device of FIG. 1.
Figure 6:
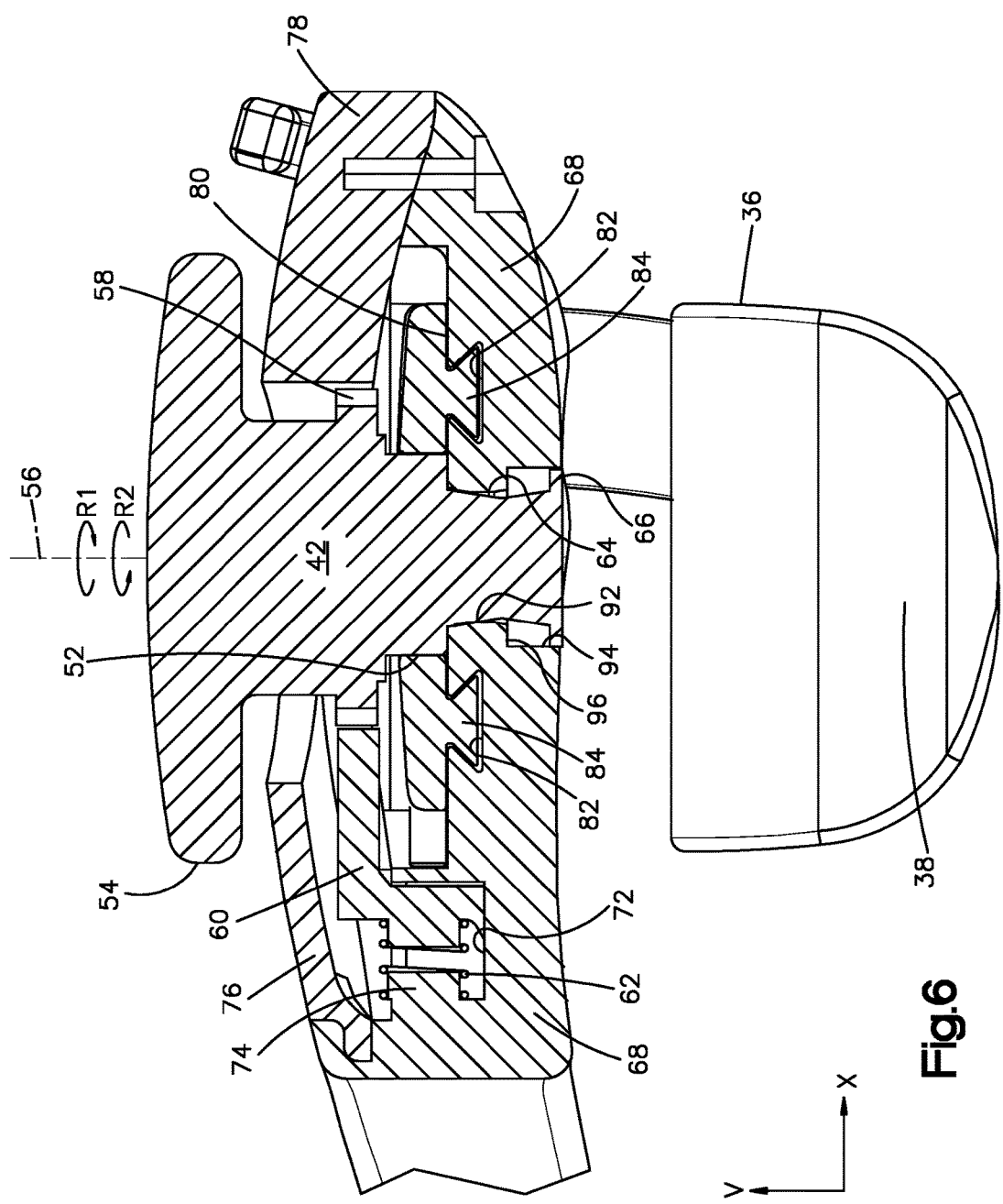
FIG. 6 is a sectional side view of a proximal portion of the bridge of the distal targeting device of FIG. 1.

Referring now to FIGS. 5 and 6, a body 68 of the bridge 20 can define a frame 70 configured to support components of the attachment device 34. An underside 71 of the frame 70 can be contoured to fit a top surface of the power tool 4. The underside 71 of the frame 70 can also be curved and concave in a vertical-lateral plane so as to enhance the fitting of the frame 70 to the tool body 21, as the tool bodies 21 of most power tools 4 have an at least partially convex and rounded profile in a vertical-lateral plane. The frame 70 can be configured to receive the camp arms 36, the actuator 42, the pawl 60, and the pawl spring 62. The frame 70 can include a pawl housing recess 72 for receiving the pawl 60 and a spring mount 74 within the recess for mounting the pawl spring 62 to the frame 70. The frame 70 can also be configured to attachably receive a pawl cover 76 and a frame cover 78 that each define an exterior surface of the bridge 20. The frame 70 can include a main support surface 80 that is configured to contact an underside of the adjustment portion 40 of each of the clamp arms 36. In this regard, the main support surface 80 can define a bearing surface for the clamp arms 36. The main support surface 80 can be substantially planar, as shown, although other configurations are within the scope of the present disclosure. The frame 70 can define a guide track for each of the arms 36. Each guide track can extend laterally and can guide movement of the arms 36 along the lateral direction Y. In the illustrated embodiment, the guide tracks each comprise a guide channel 82 recessed into the bridge body 68 from the main support surface 80. The guide channels 82 can each be configured to receive a corresponding guide protrusion 84 on the underside of the adjustment portions 40 of the arms 36. The guide channels 82 and guide protrusions 84 can have corresponding dovetail profiles in a vertical-longitudinal plane, which profiles are configured to prevent the arms 36 from moving along the vertical and/or longitudinal directions Z, X with respect to the frame 70 during adjustment of the arm distances D1, D2. The frame 70 can also define pair of abutment shoulders 86 at the lateral sides of the bridge body 68. The abutment shoulders 86 can be configured to contact abutment protrusions 88 extending outwardly from the adjustment portions 40 of the arms 36 opposite the rack teeth 46. In this manner, lateral translation of the clamp arms 36 can be limited as needed. It is to be appreciated that the bridge 20 can be provided in a kit that includes interchangeable clamp arms 36 of various sizes and/or various inner surface 38 configurations for further adapting the bridge 20 to power tools of various sizes and/or shapes.

The frame 70 can define a vertical bore 90 for receiving the stem 64 of the actuator 42. The vertical bore 90 can have an upper bore portion 92 and a lower bore portion 94 having a wider diameter than the upper bore portion 92 so as to define a shoulder 96 therebetween. As shown in FIG. 6, the upper and lower bore portions 92, 94 can be configured so that the bottom flange 66 of the actuator 42 can translate vertically within the lower bore portion 94 but is prevented by interference with the shoulder 96 from translating upward into the upper bore portion 92. In FIG. 6, the actuator 42 is shown in a first vertical position with respect to the frame 70, with the flange 66 at the bottom of the vertical bore 90, the pinion 50 intermeshed with the rack teeth 46, and the pawl 60 engaged with the ratchet teeth 58. It is to be appreciated that, to disengage the actuator 42, the physician can move the actuator 42 to a second vertical position with respect to the frame 70 by pulling upward on the knob 54 until the flange 66 abuts the shoulder 96, placing the actuator 42 in the second vertical position. In the second vertical position, the pinion 50 can be vertically spaced from the rack teeth 46 and the ratchet teeth 58 can be vertically spaced from the pawl 60. From the second position, to move the pinion 50 and ratchet teeth 58 into engagement with the rack teeth 46 and the pawl 60, respectively, the physician can depress the knob 54.

It is to be appreciated that the frame 70 and actuator 42 can collectively comprise a position locking feature that can be actuated to retain the actuator 42 in either the first or second vertical position. For example, the position locking feature can be configured such that the physician can pull upward on the knob 54 to move the actuator 42 to the second vertical position and then can lock the actuator 42 therein by rotating the knob 54 a quarter turn in one of the first or second rotational directions R1, R2. To unlock the actuator 42 from the second vertical position, the physician can rotate the knob 54 a quarter turn in the other rotational direction R2, R1 and can then depress the knob 54 so the actuator 42 moves to the first vertical position. Other position locking functionalities are within the scope of the present disclosure. In additional embodiments, the attachment device 34 can include a biasing element, such as a spring element, that can be disposed within the lower bore portion 94 and can abut the shoulder 96 and the bottom flange 66, for example, in a manner biasing the actuator 42 in the first vertical position.

As shown in FIG. 5, the frame 70 can also define a side recess 98 in one of the lateral sides of the frame 70 and a lateral slot 100 that extends inwardly from the side recess 98 and is open to the vertical bore 90. The lateral slot 100 can include an upper slot portion 102 that is laterally coextensive with the upper bore portion 92 and a lower slot portion 104 that is laterally coextensive with the lower bore portion 94. The lower slot portion 104 can be wider than the upper slot portion 102 and can be configured to receive the flange 66. In this manner, the actuator 42 can be inserted laterally into the vertical bore 90 through the lateral slot 100, with the flange 66 passing through the lower slot portion 104 and the stem 64 passing through the upper slot portion 102.

The attachment device 34 can include an insert, such as a locking clip 106, configured to retain the actuator 42 with the vertical bore 90. The locking clip 106 can define a protrusion 107 configured to extend within the lateral slot 100. The protrusion can also define a portion of each of the upper bore portion 92 and the lower bore portion 94 once fully inserted in the lateral slot 100. The locking clip 106 can also define a portion of one or more of the guide channels 82. The locking clip 106 can also define a first mounting formation 108, and the opposite lateral side of the frame 70 can define a second mounting formation 109. The first and second mounting formations 108, 109 can be configured to receive a corresponding mounting feature on an underside of the frame cover 78 for affixing the frame cover 78 to the frame 70.

Figure 10:
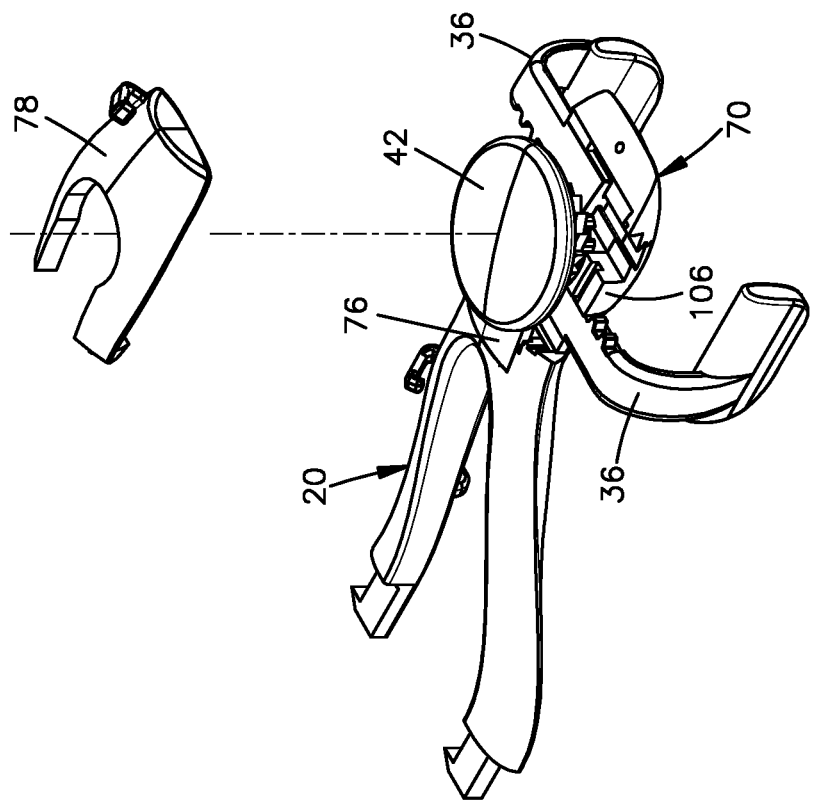
FIG. 10 is a partial exploded view of the bridge of FIG. 5, wherein a fourth step of assembling the attachment device is shown according to the example assembly sequence.
Figure 9:
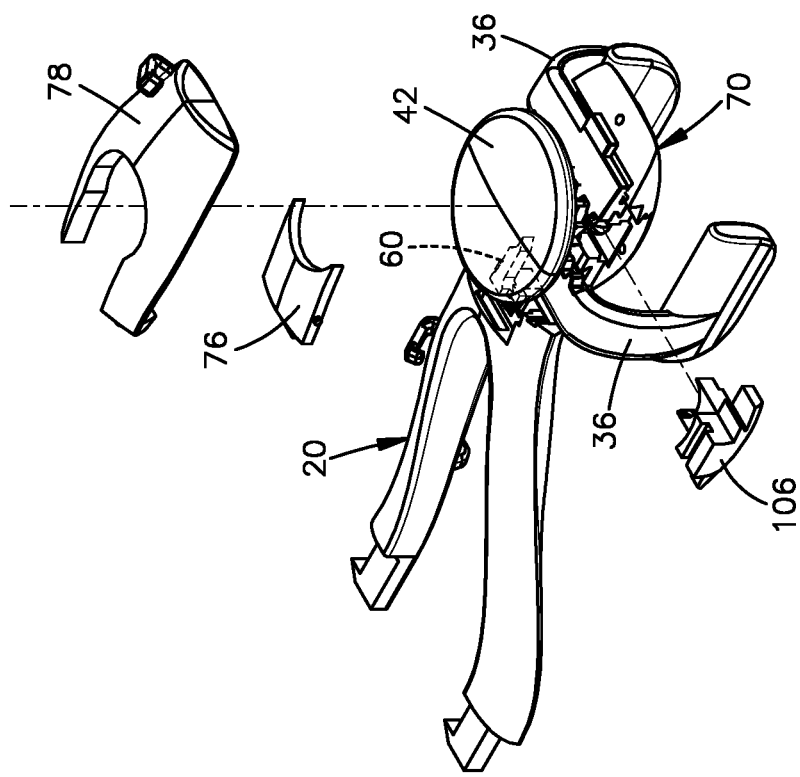
FIG. 9 is a partial exploded view of the bridge of FIG. 5, wherein a third step of assembling the attachment device is shown according to the example assembly sequence.

With reference to FIGS. 7 through 11, assembly of the attachment device 34 of the bridge 20 will now be described according to an example assembly sequence. As shown, in FIG. 7, the clamp arms 36 can be inserted laterally into the frame 70 so that the undersides of the adjustment portions 40 of the arms 36 contact the main support surface 80 and the guide protrusions 84 of the arms 36 extend within the guide channels 82 of the frame 70. Referring now to FIG. 8, the actuator 42 can be inserted within the vertical bore 90. As described above, the actuator 42 can be inserted laterally through the lateral slot 100 and into the vertical bore 90. During lateral insertion of the actuator 42, the actuator 42 can be in the second vertical position, whereby the pinion 50 and the ratchet teeth 58 avoid interference with the rack teeth 46 and the pawl 60, respectively. Referring now to FIG. 9, the pawl 60 and the pawl spring 62 can be mounted within the pawl housing recess 72. Referring to FIG. 10, the pawl cover 76 can be attached to the frame 70. The locking clip 106 can also be inserted laterally into the side recess 98 so that the protrusion 107 extends within the lateral slot 100 and completes the upper and lower bore portions 92, 94 of the vertical bore 90. In this manner, the locking clip 100 can lock the actuator 42 to the bridge body 68. Referring now to FIG. 11, the frame cover 78 can be attached to the frame 70. It is to be appreciated that other sequences of assembling the attachment device 34 are within the scope of the present disclosure.

With continued reference to FIG. 11, the bridge 20 can include one or more wire brackets 110 for retaining electrical wires, cords, or cables of the distal targeting device 2. The distal ends 30 of the branches 28 can include one or more couplers 112 for coupling with the field generator 14. As shown, the couplers 112 can each include a coupler base 114 extending distally from the associated branch 28. The couplers 112 can also each define a prong 116 extending laterally from the coupler base 114. Each prong 116 can define a proximal surface 118 extending orthogonally from the coupler base 114 and a tapered surface 120 extending from the proximal surface 118 to a distal surface 122 of the coupler base 114. The couplers 112 can be configured to engage a linkage of the field generator 14, as set forth below.

Figure 12:
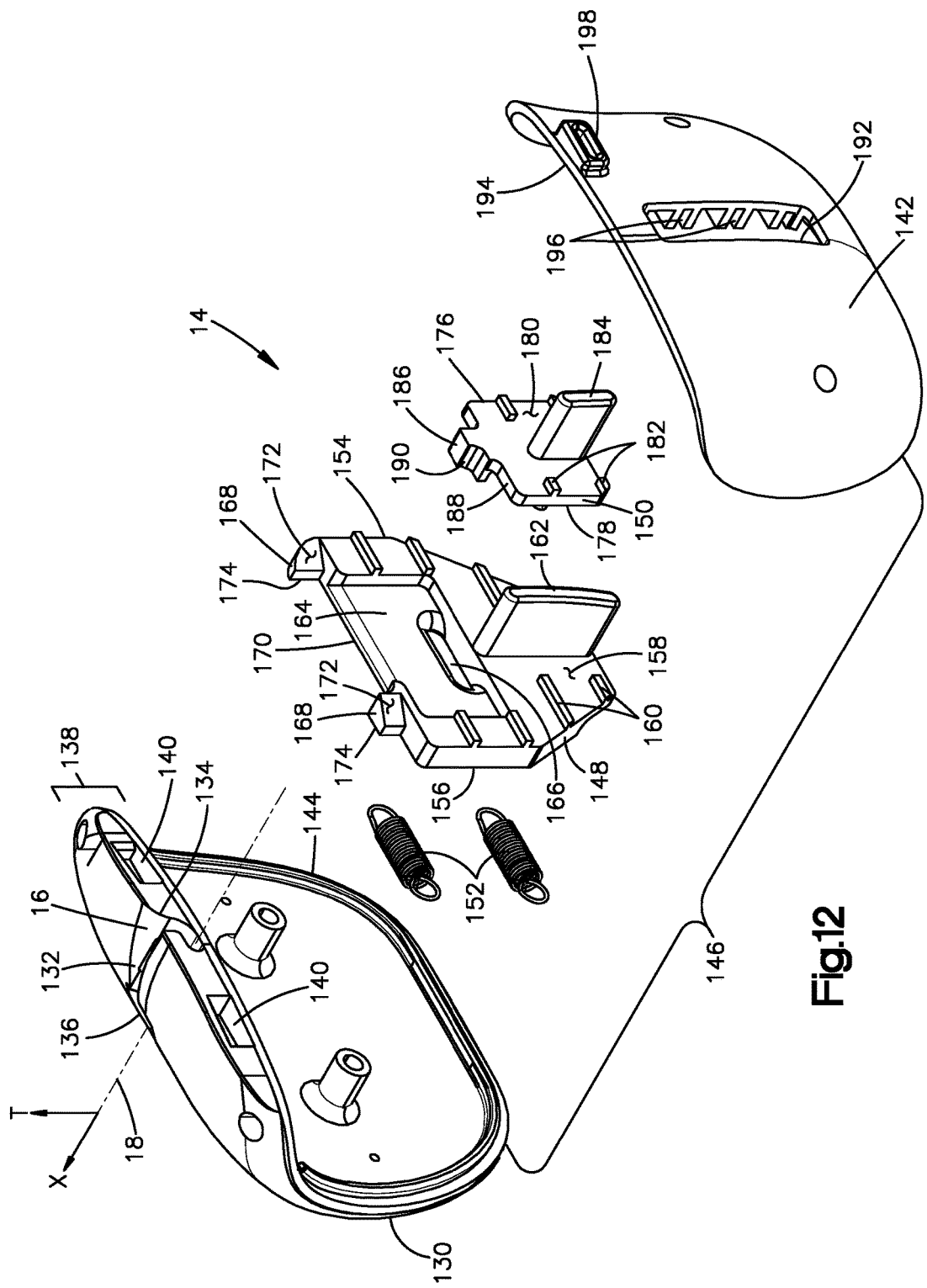
FIG. 12 is an exploded view of a field generator of the distal targeting device of FIG. 1.

Referring now to FIG. 12, the field generator 14 can include a front housing 130 containing field generator circuitry. The front housing 130 can include at least a portion of the coupling element 16 configured to receive a portion of the shaft 6. The coupling element 16 can at least partially define an opening 132 having an opening proximal end 134 and an opening distal end 136 spaced from the opening proximal end 134 in the distal direction. The opening 132 is open in a transverse direction T to an exterior of the field generator 14. The transverse direction T can be any direction that is substantially orthogonal to the longitudinal direction X. As used herein, the term "transversely" means along a transverse direction T. The opening 132 allows the shaft 6 to be inserted transversely into the coupling element 16 of the field generator 14. In this manner, the shaft 6 can be inserted within the field generator 14 without the distal or proximal ends 12, 10 of the shaft 6 passing through the opening 16. This greatly simplifies the process of inserting the shaft 6 into the field generator 14, which, in prior art distal targeting devices, can require inserting nearly the entire length of the shaft axially through the opening either distal-end-first or proximal-end-first. The opening 132 can be located at a top portion 138 of the front housing 130, as opposed to a central region of the field generator 14. However, the opening 132 can extend to the central region of the field generator 14 in other embodiments. The top portion 138 of the front housing 130 can also define a pair of receptacles 140 for receiving the couplers 112 at the distal ends 30 of the branches 28 of the bridge 20, as set forth in more detail below.

The field generator 14 can include a rear housing cover 142 configured to couple to a back side 144 of the front housing 130 so as to define a rear housing compartment 146 therebetween. The field generator 14 can include a linkage 148 and a retainer 150 within the rear housing compartment 146. The linkage 148 can be configured to latch with the couplers 112 of the bridge 20. The retainer 150 can be configured to engage the shaft 6 so as to retain the shaft 6 within the opening 132. The field generator can include biasing elements, such as coil springs 152, that are configured to bias the linkage 148 and the retainer 150, respectively, into respective biased positions. The rear housing cover 142 can be configured for releasable attachment with the front housing 130. In this manner, the field generator 14 can be disassembled, or at least partially disassembled, as needed, such as for cleaning, maintenance, and/or refurbishment, by way of non-limiting examples.

The linkage 148 can have a substantially plate-like body 154 having a front surface 156 and a rear surface 158 spaced from each other along the longitudinal direction X. The linkage body 154 can define protrusions, such as lateral guide rails 160, extending proximally from the rear surface 158. The linkage 148 can also include a depressor, such as a first push tab 162 extending proximally from the rear surface 158. The push tab 162 can be configured to allow a physician to move the linkage 148 laterally away from the linkage biased position to a linkage depressed position. The linkage body 154 can define a recess 164 in the rear surface 158 and an aperture 166 extending distally through the linkage body 154 from the recess 164. The linkage 148 can include a pair of latches 168 extending from a top surface 170 of the linkage body 154. Each of the latches 168 can define a tapered proximal surface 172 and a distal surface 174. The latches 168 can be configured to latch with the couplers 112 of the bridge 20, as more fully described below.

The retainer 150 can have a substantially plate-like body 176 having a front surface 178 and a rear surface 180 spaced from each other along the longitudinal direction X. The retainer 150 can be configured to be at least partially seated within the recess 164 in the rear surface 158 of the linkage 148. The retainer body 176 can define protrusions, such as lateral guide rails 182, extending proximally from the rear surface 180. The retainer 150 can also include a depressor, such as a second push tab 184 extending proximally from the rear surface 180. The second push tab 184 can be configured to allow a physician to move the retainer 150 laterally away from the retainer biased position to a retainer depressed position. The retainer 150 can include a shaft mount 186 extending from a top surface 188 of the retainer body 176. The shaft mount 186 can extend distally so as to overlie the top surface 170 of the linkage body 154. The shaft mount 186 can define a bearing surface 190 configured to stabilize a bearing portion of the shaft 6 when the shaft 6 is fully inserted within the opening 132 and the retainer 150 is in the retainer biased position.

With continued reference to FIG. 12, the rear housing cover 142 can define an aperture 192 through which the first and second push tabs 162, 184 can extend. A front surface 194 of the rear housing cover 142 can define guide slots 196 elongated along the lateral direction Y. The guide slots 196 are configured to receive the lateral guide rails 160, 182 of the linkage 148 and the retainer 150, respectively, so as to guide lateral movement of the linkage 148 and the retainer 150 between their respective biased and depressed positions. The rear housing cover 142 can also include a socket, such as an electrical socket 198, for coupling the field generator circuitry to a one or more electrical wires, cords, or cables.

Figure 13:
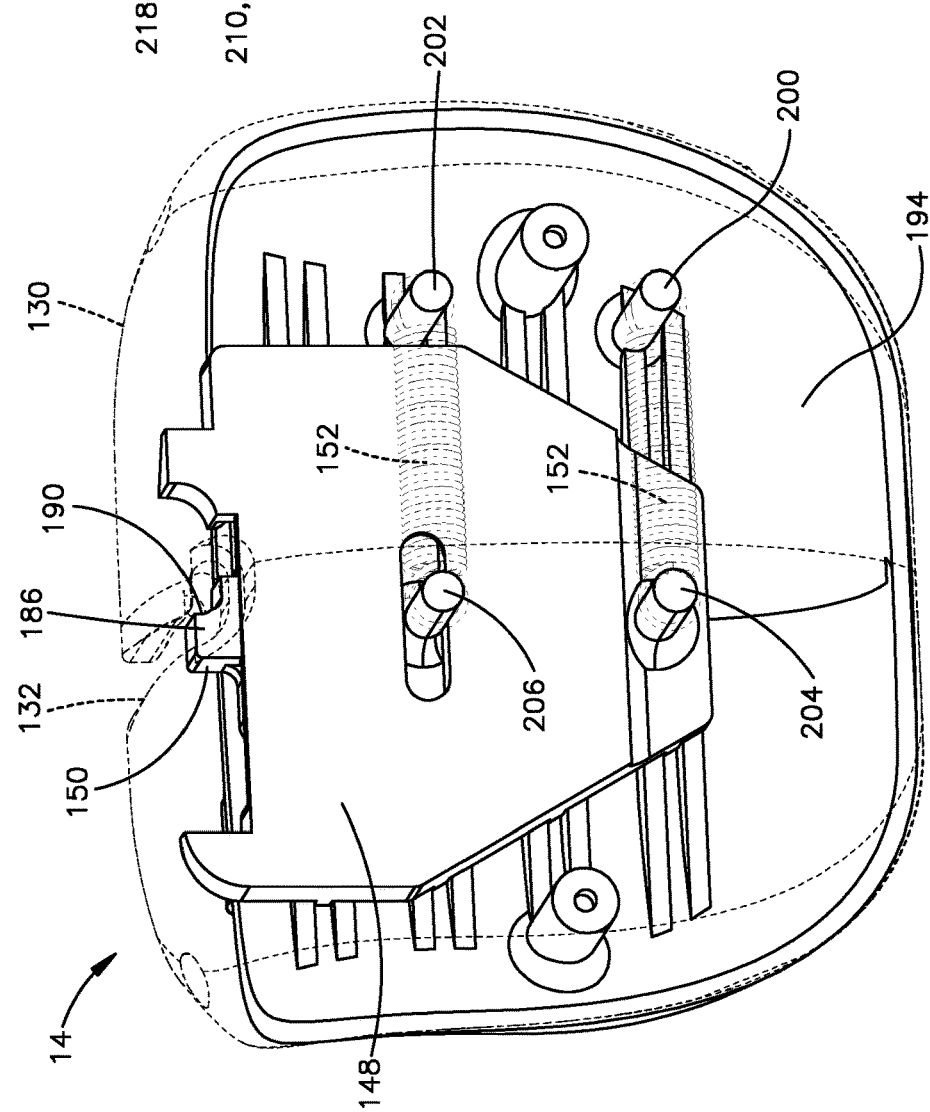
FIG. 13 is a rear, partially transparent perspective view of the assembled field generator of FIG. 12.

Referring now to FIG. 13, a front perspective view of the field generator 14 is shown with the front housing 130 in a transparent view to illustrate the linkage 148 and the retainer 150 coupled to the rear housing cover 142. The linkage 148 and the retainer 150 are each shown in FIG. 13 in their respective biased positions. A first mounting post 200 and a second mounting post 202 can extend distally from the front surface 194 of the rear housing cover 142. A third mounting post 204 can extend distally from the front surface 156 of the linkage 148. A fourth mounting post 206 can extend distally from the front surface 194 of the retainer 150 and through the aperture 166 of the linkage 148. The first and third mounting posts 200, 204 can be substantially laterally aligned and can mount opposite ends of one of the coil springs 152. Similarly, the second and fourth mounting posts 202, 206 can be substantially laterally aligned and can mount opposite ends of the other of the coil springs 152. The coil springs 152 can be tension springs configured to pull the linkage 148 and the retainer 150 toward their respective biased positions.

Figure 14:
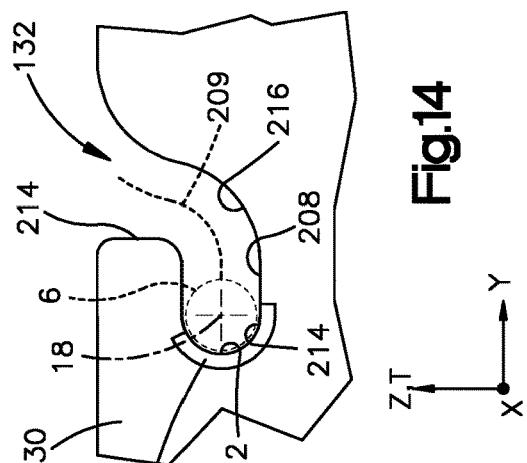
FIG. 14 is a partial sectional end view of a coupling element of the field generator of FIG. 12, showing a slot for receiving a shaft of the power tool.

Referring now to FIG. 14, the opening 132 can be a slot 208 defined by the coupling element 16 of the field generator 14. The slot 208 can define an insertion path, also referred to as an insertion axis 209, for the shaft 6. The insertion axis 209 can have linear and/or curved segments. The insertion axis 209 can also extend substantially entirely along transverse directions T. Stated differently, the insertion axis 209 can be such that any line extending between any two points on the insertion axis 209 will extend substantially transverse to the longitudinal diction X. An internal end 210 of the slot 208 can define a bearing surface 212 configured to stabilize a bearing portion of the shaft 6 during operation of the power tool 4. The bearing surface 212 can be characterized as the "shaft seat" or simply the "seat" of the field generator 14. Accordingly, an internal end of the insertion axis 209 can coincide with the shaft axis 18 when the shaft 6 is fully seated within the slot 208. As shown, the seat can be offset from a geometric center of the field generator 14, at least with respect to a transverse direction T, such as the vertical direction Z. In this manner, the seat can be located near the top of the field generator 14, allowing ease of insertion for the shaft 6 therein. In other embodiments, however, the seat can be located substantially at the geometric center of the field generator 14 (or at least at the geometric center of the field generator circuitry). As shown in FIG. 14, the slot 208 can include one or more straight portions 214 and one or more curved portions 216.

The bearing surface 212 can be defined by a bearing 218 located at the internal end 210 of the slot 208. In some embodiments, the bearing 218 can comprise a layer of low-friction material. The bearing surface 212 can be finished to have a reduced surface finish roughness so as to reduce friction between the bearing surface 212 and the shaft 6. In other embodiments, the bearing 218 can include active bearing elements, such as a plurality of roller bearings or ball bearings, dispersed along the bearing surface 212. In yet other embodiments, the bearing surface 212 can be defined by the field generator housing itself, such as by the front housing 130, for example. In further embodiments, the field generator 14 can employ a lubrication system to lubricate the bearing surface for reducing friction with the shaft 6 during operation. It is to be appreciated that other bearing features for the shaft and/or the coupling element 16 of the field generator 14 are within the scope of the present disclosure.

Figure 15:
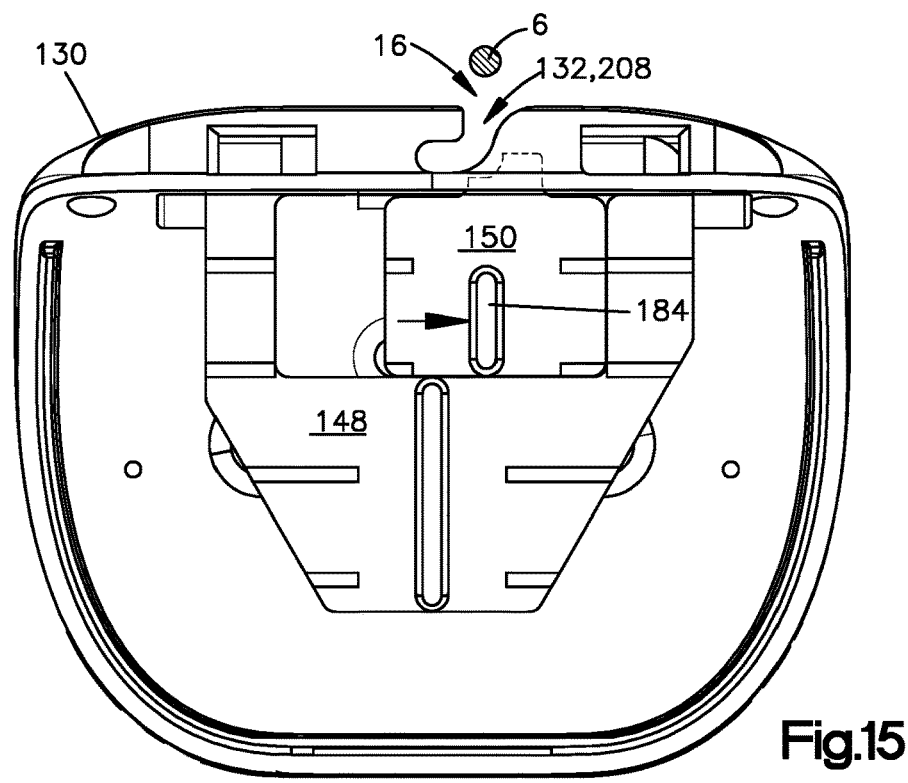
FIG. 15 is a rear view of the field generator of FIG. 12, with a rear housing cover of the field generator removed and a shaft mount shown in an open position.
Figure 16:
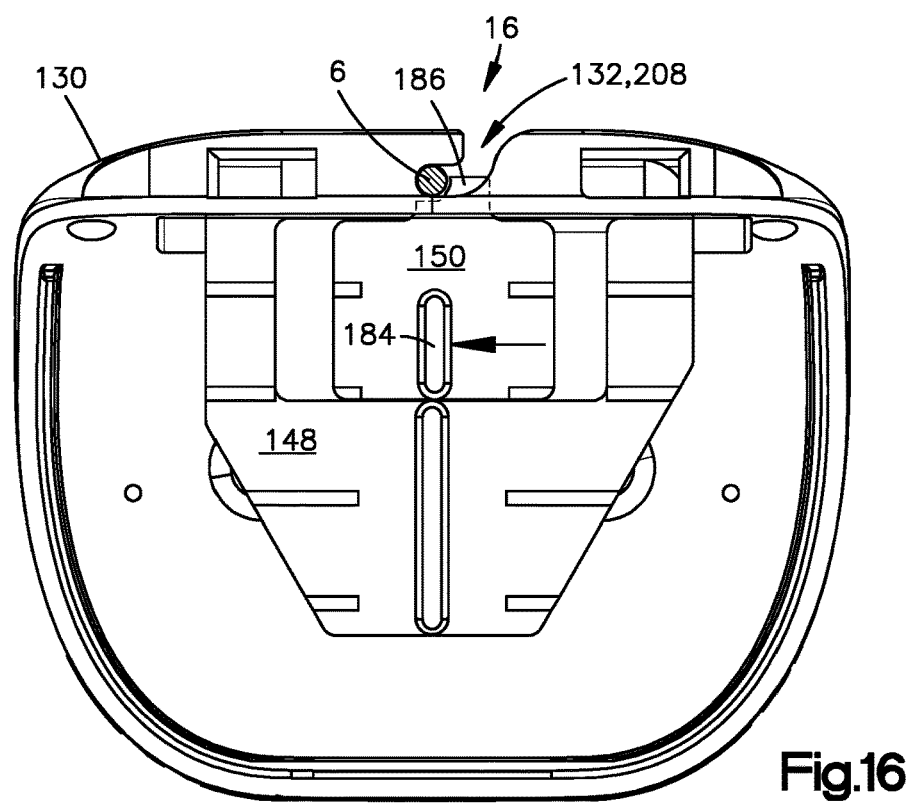
FIG. 16 is a rear view similar to that of FIG. 15, showing the shaft mount in a closed position.
Figure 17:
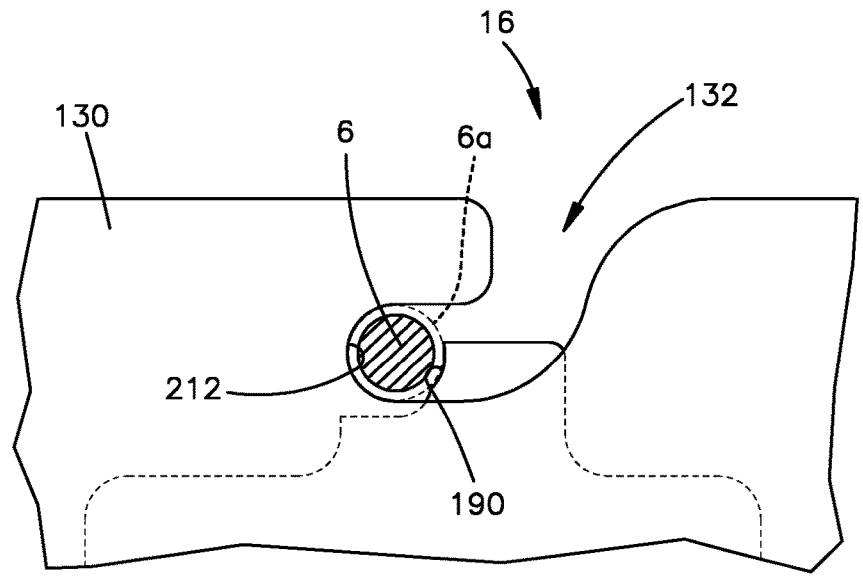
FIG. 17 is a partial sectional end view of the coupling element of FIG. 14, showing the shaft fully seated in the slot and the shaft mount in the closed position.

Referring now to FIG. 15, in the illustrated embodiment, to insert the shaft 6 within the slot 208, the physician can use the second push tab 184 to depress the retainer 150 to the depressed retainer position, as shown. With the shaft 6 inserted in the slot 208 and the retainer 150 depressed into the depressed retainer position, the shaft 6 is unrestrained by the retainer 150. When the physician released the second push tab 184, the retainer 150 is biased to the retainer biased position, as shown in FIGS. 16 and 17. In the retainer biased position, the shaft mount 186 can be in close proximity, and can optionally abut, the shaft 6. In this retainer biased position, the retainer 150 retains the shaft in a fully seated position. As with the bearing surface 212 of the slot 208, the bearing surface 190 of the retainer 150 can employ one or more of a layer of low-friction material, surface finishing, active bearing elements, lubrication, any combination of the foregoing, or any other type of bearing features for reducing friction with the shaft 6. The shaft 6 and the coupling element 16 can optionally be cooperatively configured such that a small gap is present between the shaft 6 and one or more of the bearing surfaces 190, 212 when the shaft is fully seated. In other embodiments, the shaft 6 and the coupling element 16 can be cooperatively configured such that, as shown in dashed lines 6a, the shaft 6 abuts, in bearing fashion, one or both of the bearing surfaces 190, 212 while being able to rotate about the shaft axis 18 in substantially unrestricted fashion. In the illustrated embodiment, with the retainer 150 in the biased retainer position, the bearing surfaces 190, 212 can substantially fix the transverse position of the shaft 6 relative to the field generator 14, which enhances the distal targeting accuracy of the distal targeting system. It is to be appreciated that the coupling element 16 can be configured to accommodate shafts within a range of diameters. It is also to be appreciated that the coupling element can be scaled larger or smaller as needed to accommodate additional shaft 6 diameters.

Figure 18:
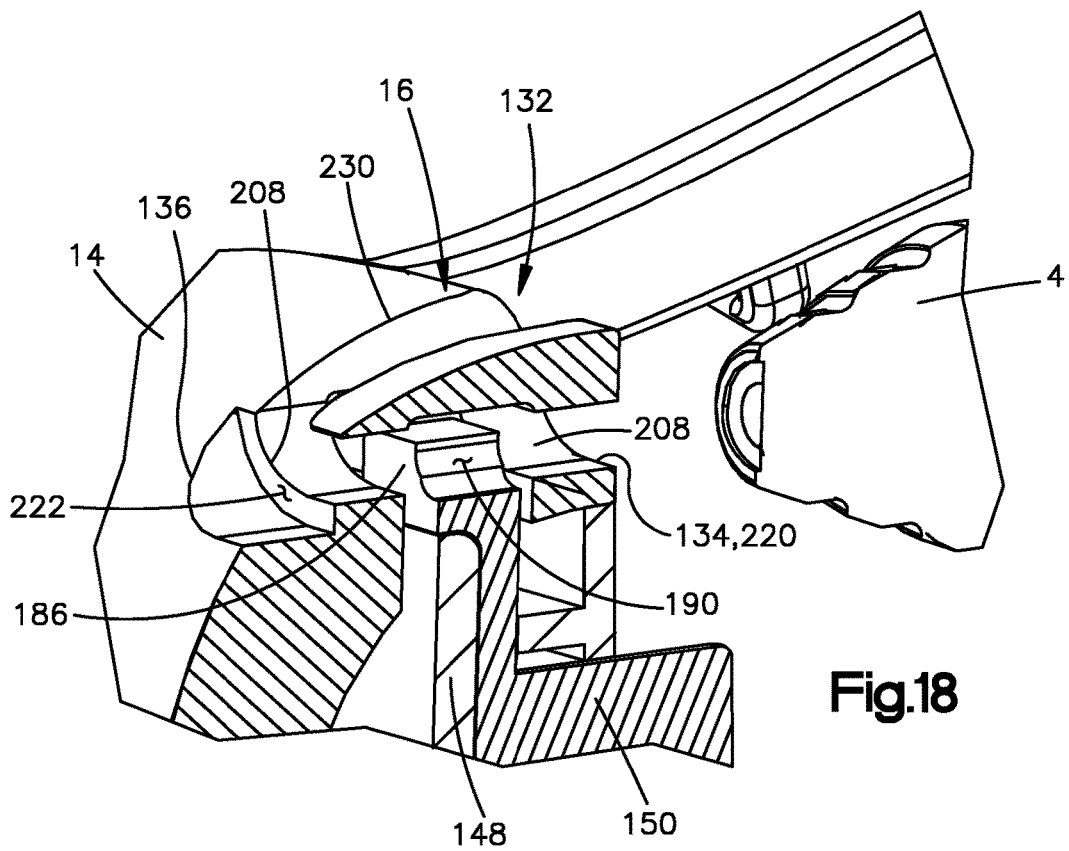
FIG. 18 is a perspective sectional side view of the coupling element of the field generator of FIG. 12.

Referring now to FIG. 18, the opening 132 of the coupling element 16 can include one or more axial retention elements configured to engage corresponding axial retention elements of the shaft. The axial retention elements of the opening 132 and the shaft 6 can be cooperatively configured to prevent axial movement of the shaft 6 relative to the field generator 14, at least when the shaft 6 is fully seated within the slot 208. As shown, the axial retention elements of the opening 132 can include one or more abutment surfaces of the coupling element 16. For example, the coupling element 16 can define a proximal abutment surface 220 and a distal abutment surface 222 spaced from the proximal abutment surface 220 in the distal direction. The proximal abutment surface 220 can be positioned at the proximal end of the opening 132. The distal abutment surface 220 can be located distally of the each of the linkage 148 and the retainer 150 yet proximally of the distal end 136 of the opening 132. One or both of the proximal and distal abutment surfaces 200, 222 can be orthogonal to the longitudinal direction X.

Figure 19:
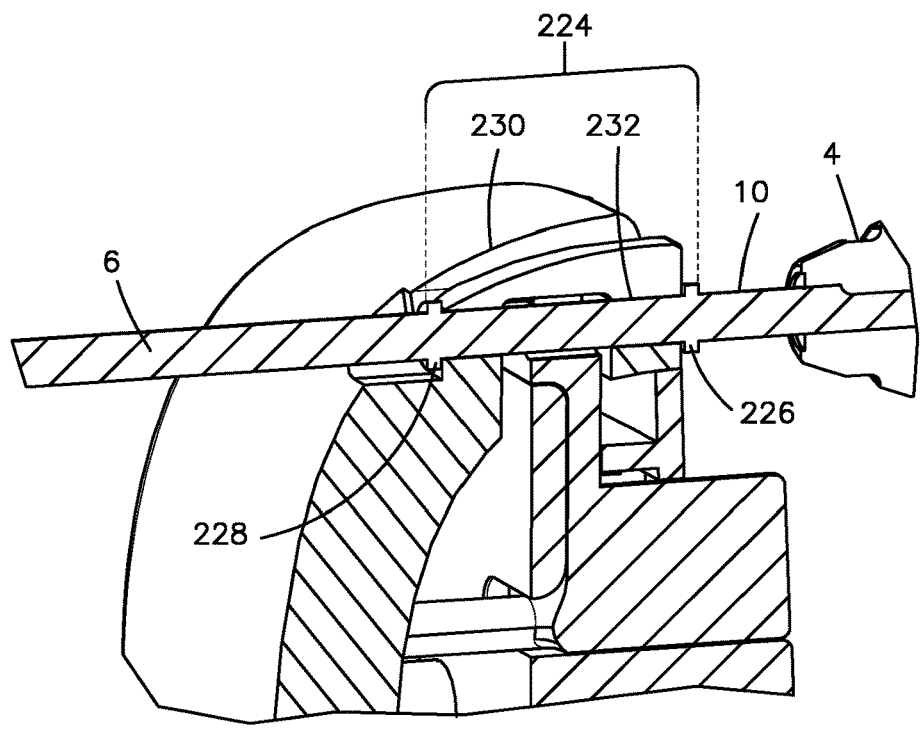
FIG. 19 is another perspective sectional side view of the coupling element with the shaft fully seated in the slot.

Referring now to FIG. 19, the shaft 6 can define a bearing portion 224 configured to extend within the opening 132 and couple with the coupling element 16 in a manner preventing axial translation of the shaft 6 relative to the field generator 14. As shown, the bearing portion 224 of the shaft can include a proximal flange 226 and a distal flange 228. The inner surfaces of the flanges 226, 228 can be longitudinally spaced from each other at a distance that is substantially equivalent to, but no less than, the longitudinal distance between the proximal and distal abutment surfaces 220, 222. In this manner, when the bearing portion 224 of the shaft 6 is fully seated within the slot 208, the abutment surfaces 220, 220 and the flanges 226, 288 can cooperatively prevent axial translation of the shaft 6 relative to the field generator. In this manner, the axial position of the shaft 6 can be substantially fixed relative to the field generator 14, which further enhances the distal targeting accuracy of the distal targeting system. A lateral edge 230 of the opening 132 can be contiguous with the each of the proximal and distal abutment surfaces 220, 222 so as to form a guide that effectively directs the flanges 226, 228 into abutment with the abutment surfaces 220, 222. The inner surfaces of one or both of the flanges 226, 228, as well as an outer surface 232 of the shaft 6 between the flanges 226, 228, can be finished to have a reduced surface finish roughness so as to reduce friction between the shaft 6 and the coupling element 16. In other embodiments, the bearing portion 224 of the shaft 6 can include one or more external layers of low-friction material to reduce friction between the shaft 6 and the coupling element 16. In yet other embodiments, the bearing portion 224 of the shaft 6 can include one or more active bearing elements, such as journal bearings, roller bearings, ball bearings, thrust bearings (for the flanges 226, 228), by way of non-limiting examples, to reduce friction between the shaft 6 and the coupling element 16.

Figure 20:
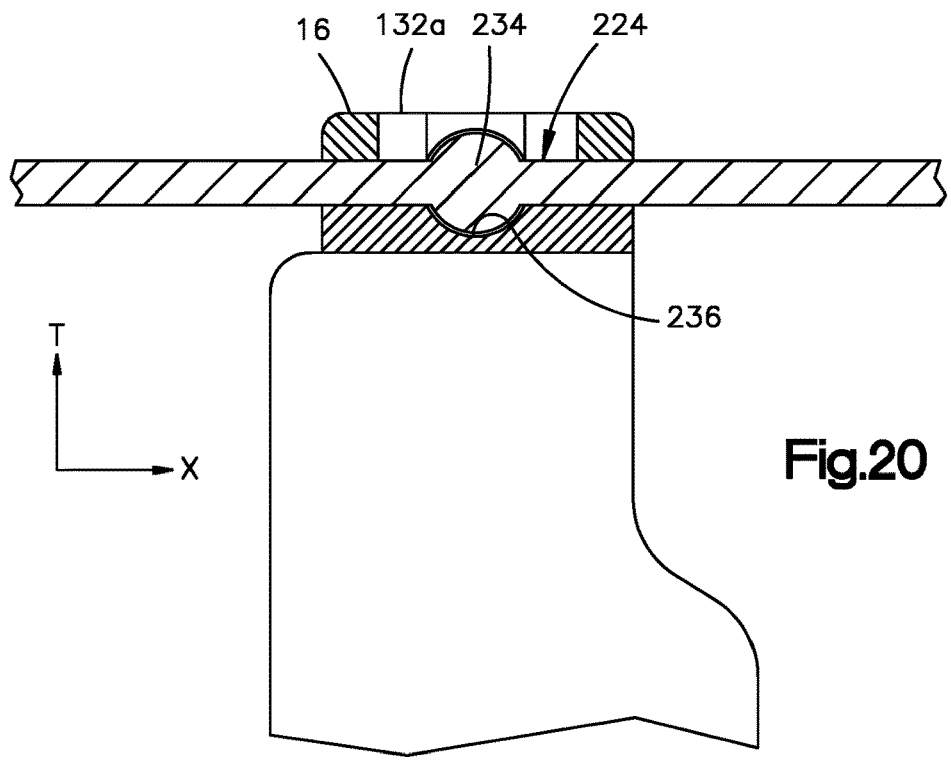
FIG. 20 is a side sectional view of a retention element for retaining a position of a shaft within a coupling element of a field generator, according to another embodiment of the present disclosure.

Referring now to FIG. 20, another embodiment of an axial retention element is shown. In this embodiment, the shaft 6 can define a ball flange 234 and the coupling element 16 can define an at least partially spherical groove 236 in which the ball flange 234 is seated. As above, the coupling element 16 defines a transverse-entry opening 132a. In other embodiments, the bearing portion 224 of the shaft 6 can define a single cylindrical flange configured to be seated within a single cylindrical recess within the coupling element 16. It is to be appreciated that other axial retention configurations for the shaft 6 are within the scope of the present disclosure.

Figure 21:
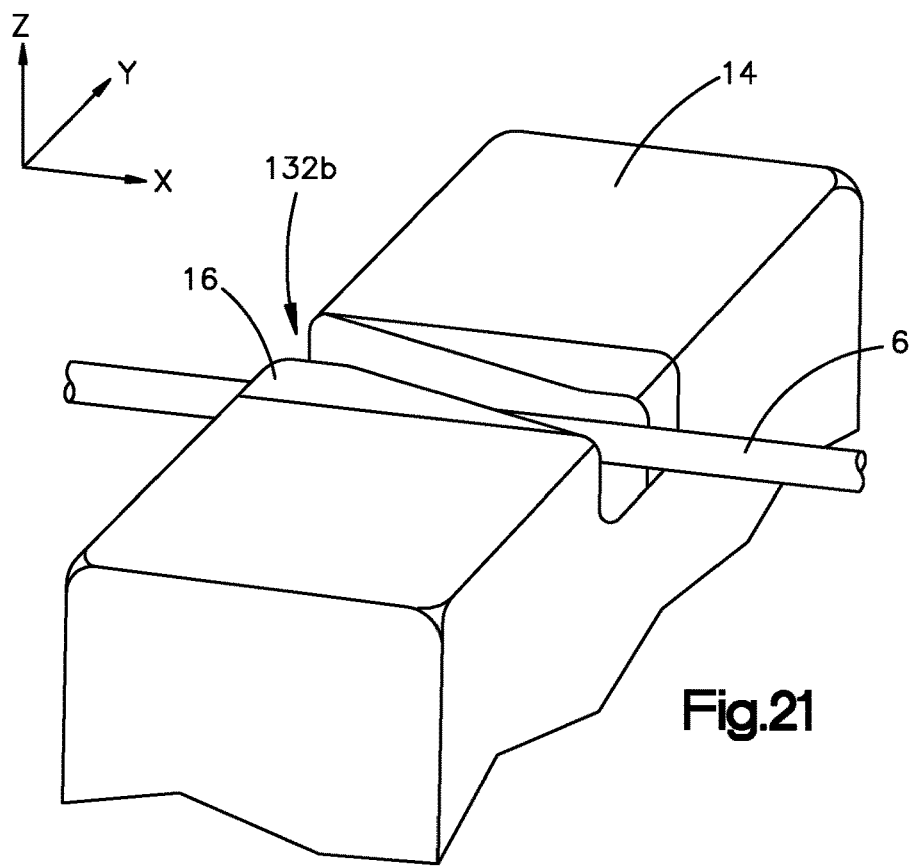
FIG. 21 is a partial front perspective view of a coupling element of a field generator, according to another embodiment of the present disclosure.
Figure 22:
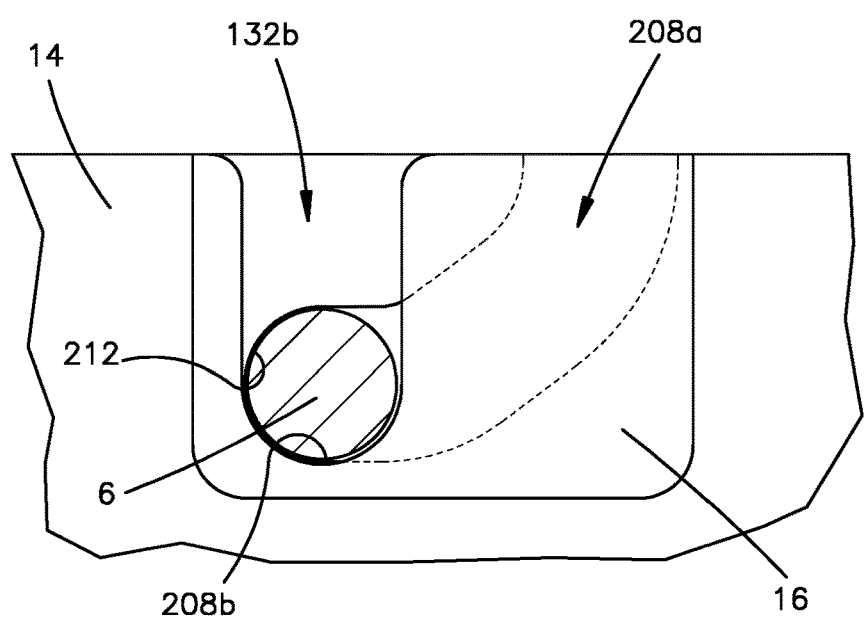
FIG. 22 is front view of the coupling element of FIG. 21.

Referring now to FIGS. 21 and 22, an example of a field generator 14 with a coupling element 16 having a partially oblique opening 132b with respect to the longitudinal direction X is shown. The partially oblique opening 132b can include an oblique upper slot portion 208a and a longitudinal lower slot portion 208b (FIG. 22). In this embodiment, the longitudinal lower slot portion 208b can define the bearing surface 212. In such an embodiment, at least a portion of the shaft 6 can enter the opening 132 at an oblique angle with respect to the longitudinal direction X. The oblique upper slot portion 208a can be configured to funnel the shaft 6 into the longitudinal lower slot portion 208b as the shaft 6 moves downwardly in the opening 132b. The partially oblique opening 132b can be characterized as a transverse-entry opening because each point on the shaft 6 can move substantially in transverse directions T as the shaft 6 is inserted within the opening 132. It is to be appreciated that other types of transverse-entry opening configurations are within the scope of the present disclosure.

Figure 23:
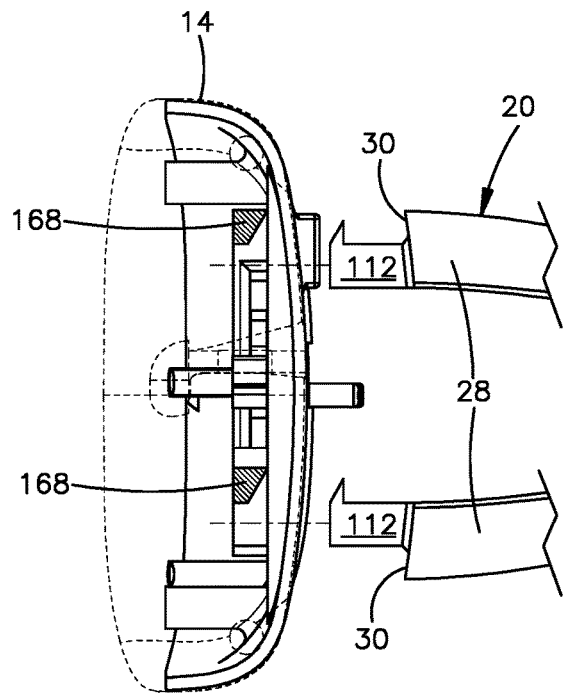
FIG. 23 is a top, partially transparent view of the field generator of FIG. 12, showing a linkage of the field generator in a biased position prior to coupling with the bridge of FIG. 11.
Figure 24:
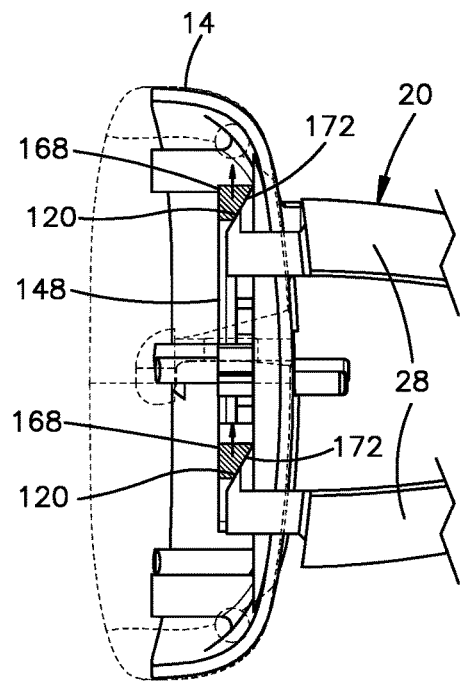
FIG. 24 is a top, partially transparent view of the field generator and the bridge of FIG. 23, showing couplers of the bridge engaged with the linkage of the field generator in a manner moving the linkage away from the biased position.
Figure 25:
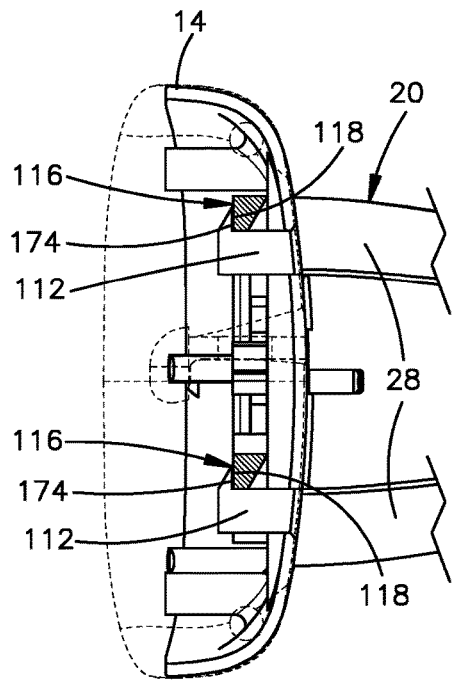
FIG. 25 is a top, partially transparent view of the field generator and the bridge of FIG. 23, showing the linkage of the field generator in a latched position with respect to the couplers of the bridge.
Figure 26:
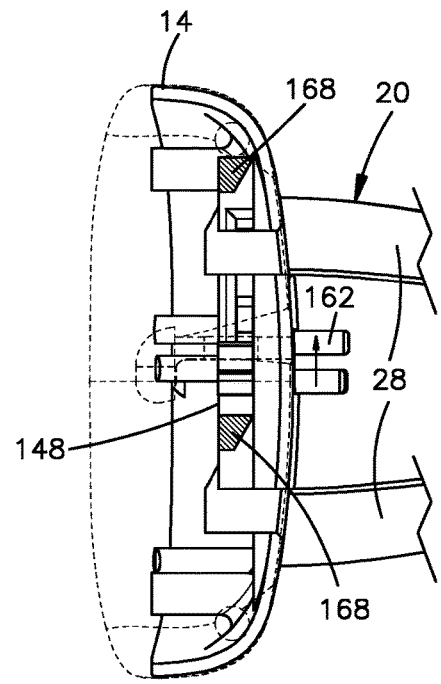
FIG. 26 is a top, partially transparent view of the field generator and the bridge of FIG. 23, showing the linkage of the field generator in a fully open position for decoupling the bridge from the field generator.

With reference to FIGS. 23 through 26, an example mode of releasably coupling the field generator 14 to the bridge 20 will now be described. As used herein, the term "releasably coupling" and its derivatives means repeatedly coupling and decoupling in a non-destructive manner. As shown in FIG. 23, the bridge 20 can be advanced distally toward the field generator 14 (or the field generator 14 can be advanced proximally toward the bridge 20) so that the couplers 112 at the distal ends 30 of the branches 28 are aligned with the receptacles 140 (FIG. 12) in the top portion 138 of the front housing 130. As shown in FIG. 24, the bridge 20 can be further advanced into the receptacles 140 so that the couplers 112 engage the associated latches 168 of the linkage 148. As the bridge 20 continues to advance distally within the receptacles 140, the distal tapered surfaces 120 of the couplers 112 engage the proximal tapered surfaces 172 of the latches 168, which causes the latches 168 to translate laterally. As shown in FIG. 25, once the prongs 116 advance distally beyond the latches 168, the linkage 148 and the latches 168 thereof are biased back to the linkage biased position, whereby the distal surfaces 174 of the latches 168 latch behind the proximal surfaces 118 of the prongs 116, causing mechanical interference in the proximal direction. In this manner, once the prongs 116 advance distally beyond the latches 168, the latches 168 and the couplers 112 rigidly couple the bridge 20 to the field generator 14. As shown in FIG. 26, to release the couplers 112 from the latches 168, the physician can depress the first push tab 162 to move the linkage 148 to the linkage depressed position, allowing the bridge 20 to be decoupled proximally from the field generator 14.

Figure 27:
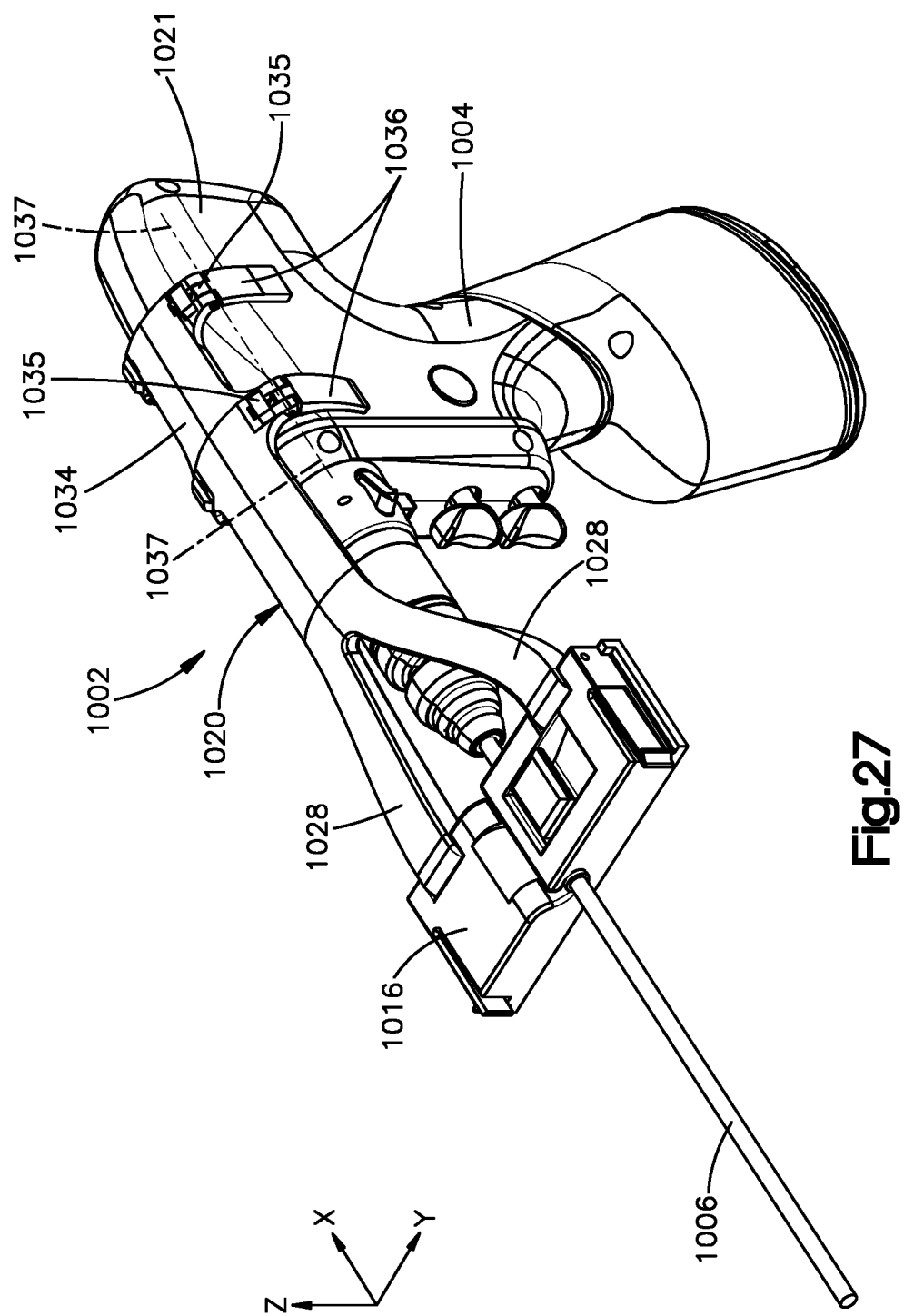
FIG. 27 is a perspective view of a distal targeting device coupled to a power tool, according to another embodiment of the present disclosure.

Referring now to FIG. 27, another embodiment of a distal targeting device 1002 is shown. The distal targeting device 1002 can be similar to the distal targeting device 2 described above. The distal targeting device 1002 can include a bridge 1020 having an attachment device 1034 that is connectable to a power tool 1004. The bridge 1020 has a pair of clamp arms 1036 configured to clasp the body 1021 of the tool 1004 in a manner substantially rigidly coupling the bridge 1020 to the power tool 1004. The clamp arms 1036 are positionable with respect to the attachment device 1034 at a distance that is adjustable so as to enable the arms 1036 to substantially rigidly clasp tool bodies 1021 having one or more of various shapes and/or sizes therebetween. The bridge 1020 can include a pair of branches 1028 that extend laterally outwardly on either side of the shaft 1006 and couple to a coupling element 1016. The coupling element 1016 can be configured to carry a field generator, although the field generator is not shown in FIG. 27.

In the present embodiment, the clamp arms 1036 can be configured as spring-hinge clamps that are configured to bias the clamp arms 1036 against the tool body 1021. One or more of the clamp arms 1036 can be coupled to the attachment device 1034 at a spring hinge 1035 defining a hinge axis 1037 substantially oriented along the longitudinal direction X. As shown, the bridge 1020 can include two (2) pairs of spring-hinge arms 1036, although, in other embodiments, the bridge 1020 can have a single pair of opposed spring-hinge arms 1036. As shown in FIGS. 28 and 29, at the spring hinges 1035, the clamp arms 1036 can each define a first spring mount 1039 facing a second spring mount 1041 defined by the attachment device 1034. The second spring mount 1041 can be located in a hinge recess 1043 defined by the attachment device 1034. A biasing element, such as a tension spring 1045, can be mounted to the first and second spring mounts 1039, 1041 in a manner biasing the clamp arms 1036 toward a fully clamped position against the tool body 1021. In this manner, as shown in FIG. 29, the clamp arms 1036 can rigidly clasp tool bodies 1021 of various sizes and/or shapes. Thus, the tension springs 1045 can be characterized as "actuators" for clamping the clamp arms 1036. The spring hinges 1035 can also define a toggle point, so that when the arms 1036 are rotated outward beyond the toggle point, the arms 1036 are biased into a fully open position O, as shown in FIG. 29. As set forth above, inner surfaces 1038 of the arms 1036 can include a layer of high-friction material for increasing the clamping grip of the arms 1036 to the tool body 1021. An underside 1071 of the attachment device 1034 can be contoured, such as by being curved and concave in a vertical-lateral plane, to fit a top surface of the power tool 1004.

Figure 30:
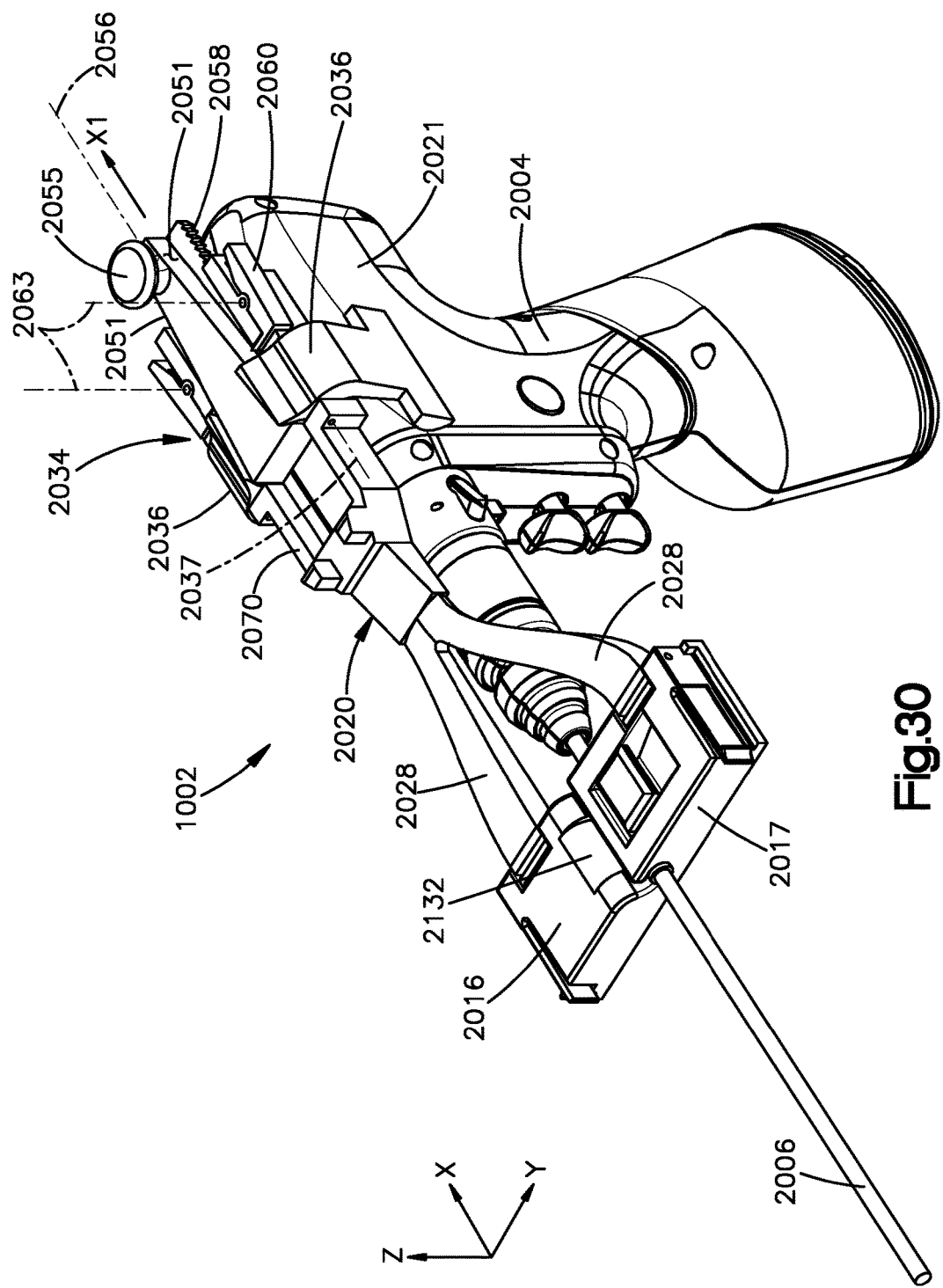
FIG. 30 is a perspective view of a distal targeting device coupled to a power tool, according to another embodiment of the present disclosure.

Referring now to FIG. 30, another embodiment of a distal targeting device 2002 is shown. The distal targeting device 2002 can be similar to the distal targeting devices 2, 1002 described above. The distal targeting device 2002 can include a bridge 2020 having an attachment device 2034 that is connectable to a power tool 2004. The bridge 2020 has a pair of clamp arms 2036 configured to clasp the body 2021 of the tool 2004 in a manner substantially rigidly coupling the bridge 2020 to the power tool 2004. The clamp arms 2036 are positionable with respect to the attachment device 2034 at a distance that is adjustable so as to enable the arms 2036 to substantially rigidly clasp tool bodies 2021 having one or more of various shapes and/or sizes. The bridge 2020 can include a frame 2070 supporting the attachment device 2034. The bridge 2020 can include a pair of branches 2028 that extend laterally outwardly on either side of the shaft 2006 and couple to a coupling element 2016. The coupling element 2016 can be configured to carry a field generator, although the field generator is not shown in FIG. 30.

Figure 31:
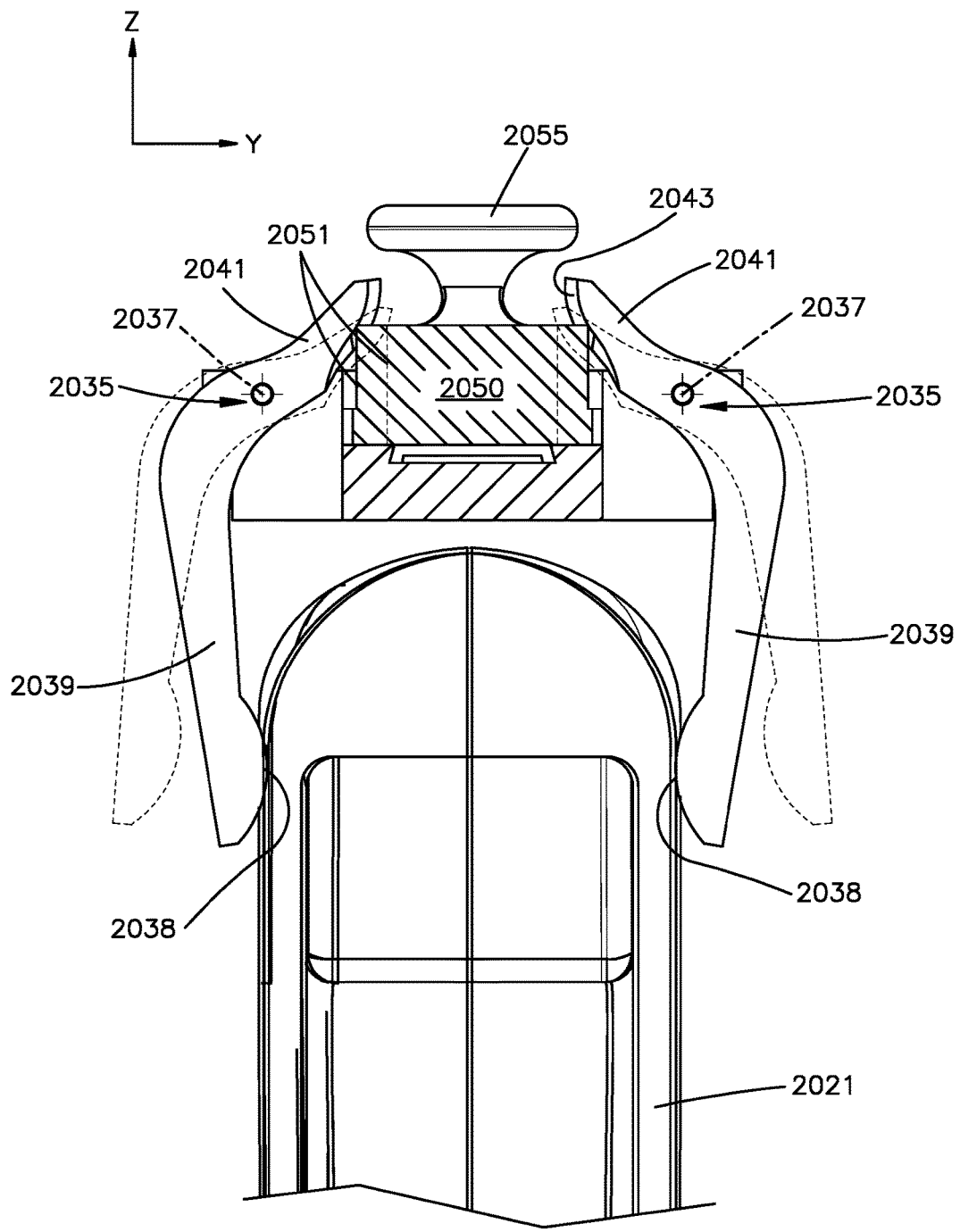
FIG. 31 is a partial sectional end view of the distal targeting device of FIG. 30, showing clamp arms of the device in a closed position, as well as in an open position in phantom lines.

Referring now to FIG. 31, the clamp arms 2036 can be coupled to the frame 2070 at respective pivot joints, such as hinges 2035. The hinges 2035 can each define a hinge axis 2037 about which the clamp arms 2036 rotate. The hinge axes 2037 can be oriented substantially along the longitudinal direction X. The clamp arms 2036 can define a first portion 2039 extending from the hinge 2035 to the tool body 2021. The first portions 2039 of the arms 2036 can define inner tool contact surfaces 2038 configured to contact the tool body 2021. As set forth above, the inner tool contact surfaces 2038 of the arms 2036 can include a layer of high-friction material for increasing the clamping grip of the arms 2036 to the tool body 2021. The clamp arms 2036 can also define a second portion 2041 extending from the hinge 2035 to an actuator, such as a translating member 2050, of the attachment device 2034. The second portions 2041 of the clamp arms 2036 can define inner actuation contact surfaces 2043 configured to engage the translating member 2050. It is to be appreciated that the attachment device 2034 can optionally include a cover (not shown), such as a top fold-over cover, so as to cover at least a portion of the translating member 2050 and the clamp arms 2036.

Referring again to FIG. 30, the translating member 2050 can be configured to translate along an axis of translation 2056 in a manner biasing the inner tool contact surfaces 2038 of the clamp arms 2036 against the tool body 2021. As shown, the axis of translation 2056 can be oriented along the longitudinal direction X, although other orientations are possible. The translating member 2050 can include a knob 2055 allowing easier manipulation of the translating member 2050. The translating member 2050 can define one or more exterior contact surfaces 2051 that are configured to engage the inner actuation contact surfaces 2043 of the arms 2036. As shown, one or more of the exterior contact surfaces 2051 of the translating member 2050 can be oblique with respect to the longitudinal direction X in a manner providing the translating member 2050 with a wedge-shaped configuration. The exterior contact surfaces 2051 can taper inwardly along the proximal direction, as shown. The inner actuation contact surfaces 2043 of one or more of the arms 2036 can also be oblique with respect to the longitudinal direction X. At least a portion of the inner actuation contact surfaces 2043 can be conical in shape so as to increase in width along the proximal direction. The exterior contact surfaces 2051 of the translating member 2050 and the inner actuation contact surfaces 2043 of the arms 2036 can be cooperatively configured such that the physician can bias the inner actuation contact surfaces 2043 laterally outward (thus hingedly biasing the inner tool contact surfaces 2038 laterally inward) by translating the translating member 2050 in a first translation direction X1. In the illustrated embodiment, the first translation direction X1 is in the proximal direction.

The attachment device 2034 can include a ratchet configured to prevent the arms 2036 from moving laterally outward after the arms 2036 are clamped onto the tool body 2021. The ratchet can include ratchet teeth 2058 linearly disposed along one or more ratchet racks on an exterior of the translating member 2050. The ratchet can include one or more pawls 2060 configured to engage the ratchet teeth 2058 in a manner allow the translating member 2050 to translate along the first translation direction X1 while impeding translation along a second translation direction X2 opposite the first translation direction X1. The one or pawls 2060 can each rotate along a pawl axis 2063. The one or pawls 2060 can each include a tab allowing the pawls 2060 to be manually disengaged from the ratchet teeth 2058.

Figure 33:
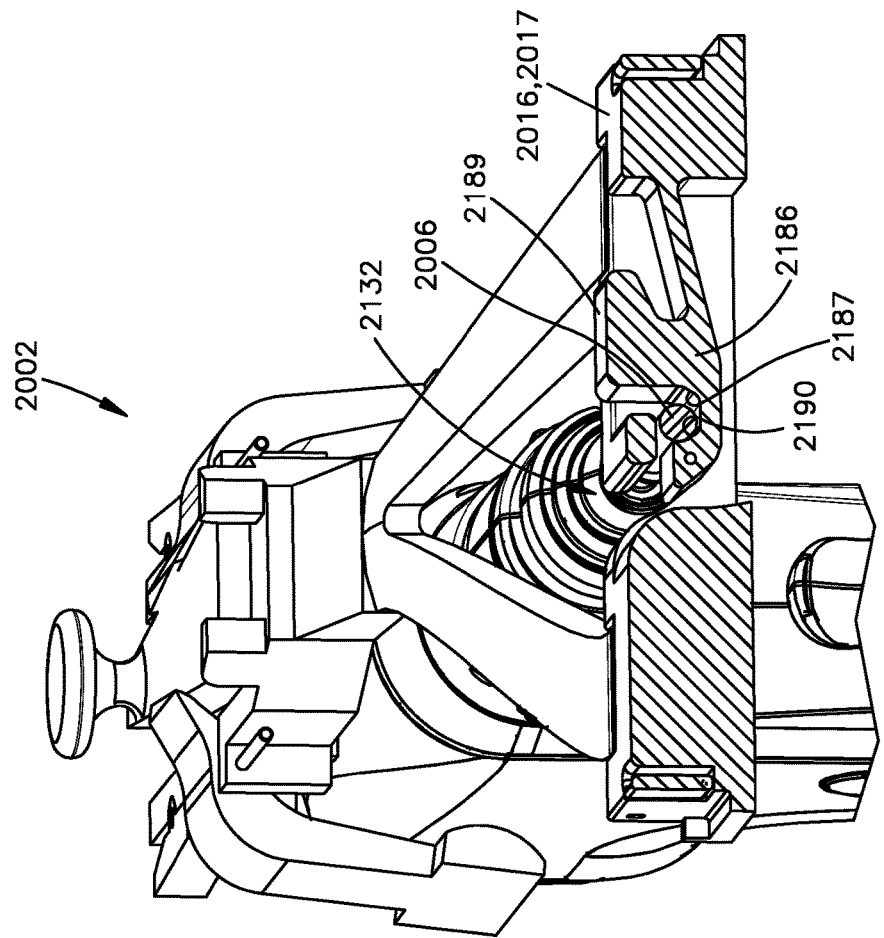
FIG. 33 is a perspective sectional view of a coupling element of the distal targeting device, taken along section line 33-33 of FIG. 30, wherein the coupling element is configured to carry a field generator.
Figure 32:
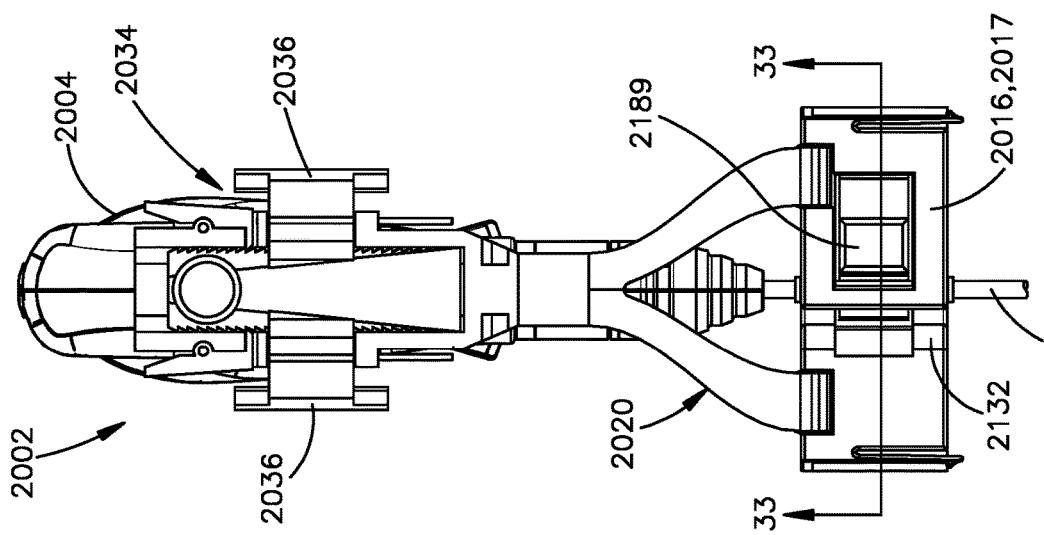
FIG. 32 is a top view of the distal targeting device of FIG. 30.

As shown in FIGS. 30, 32, and 33, the coupling element 2016 of the present embodiment can define a mounting bracket 2017 configured to releasably mount with a field generator. The coupling element 2016 can define a transverse-entry opening 2132 similar to those described above. Referring now to FIG. 33, the coupling element 2016 can include a shaft mount 2186 having a groove 2187 in which the shaft 2006 can be seated when the shaft 2006 is also fully seated within the opening 2132. The shaft mount 2186 can include a bearing surface 2190 within the groove 2187. In the present embodiment, the shaft mount 2186 can be a compliant linkage of the coupling element 2016. The shaft mount 2186 can include a button 2189 that can be manually depressed to flex the shaft mount 2186, such as downward, in a manner allowing the shaft 2006 to be guided by the opening 2132 into the groove 2187. When the button 2189 is released, the shaft mount 2186 flexes, such as upward, to a position at which the shaft 2006 is fully seated within the groove 2187 and in engagement with the bearing surface 2189.

It is to be appreciated that the coupling elements 16, 1016, 2016 disclosed herein represent non-limiting examples of coupling elements that can be employed for transverse-entry coupling of the shaft to the field generator.

Figure 34:
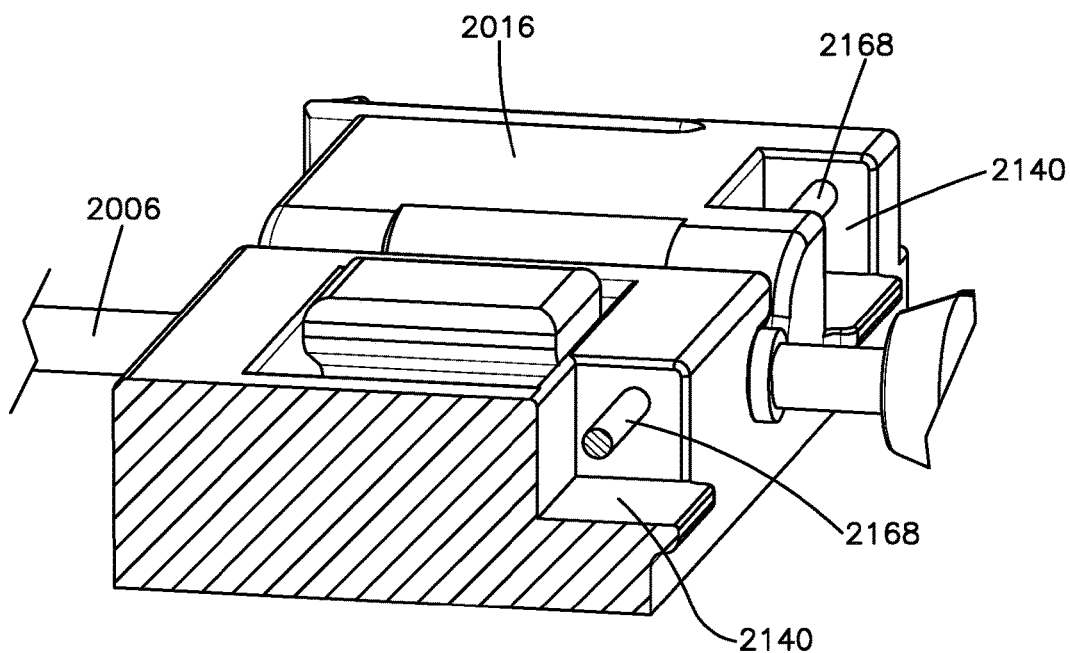
FIG. 34 is another sectional view of the coupling element of FIG. 33.
Figure 35:
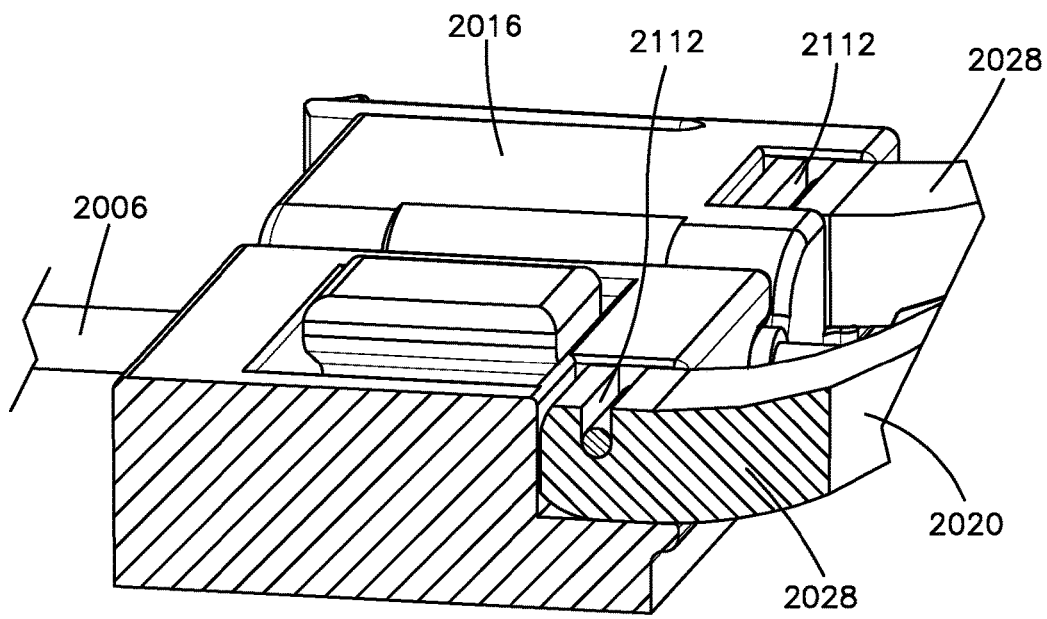
FIG. 35 shows the sectional view of the coupling element of FIG. 34, with the coupling element coupled to branches of a bridge of the distal targeting device of FIG. 30.

Referring now to FIGS. 34 and 35, the coupling element 2016 can include a linkage, such as one or more transverse pins 2168 extending within a pair of receptacles 2140 on a proximal side of the coupling element 2016. The distal ends of the branches can define coupler recesses 2112 configured to receive the transverse pins 2186 in a manner substantially rigidly coupling the bridge 2020 to the coupling element 2016.

Figure 36:
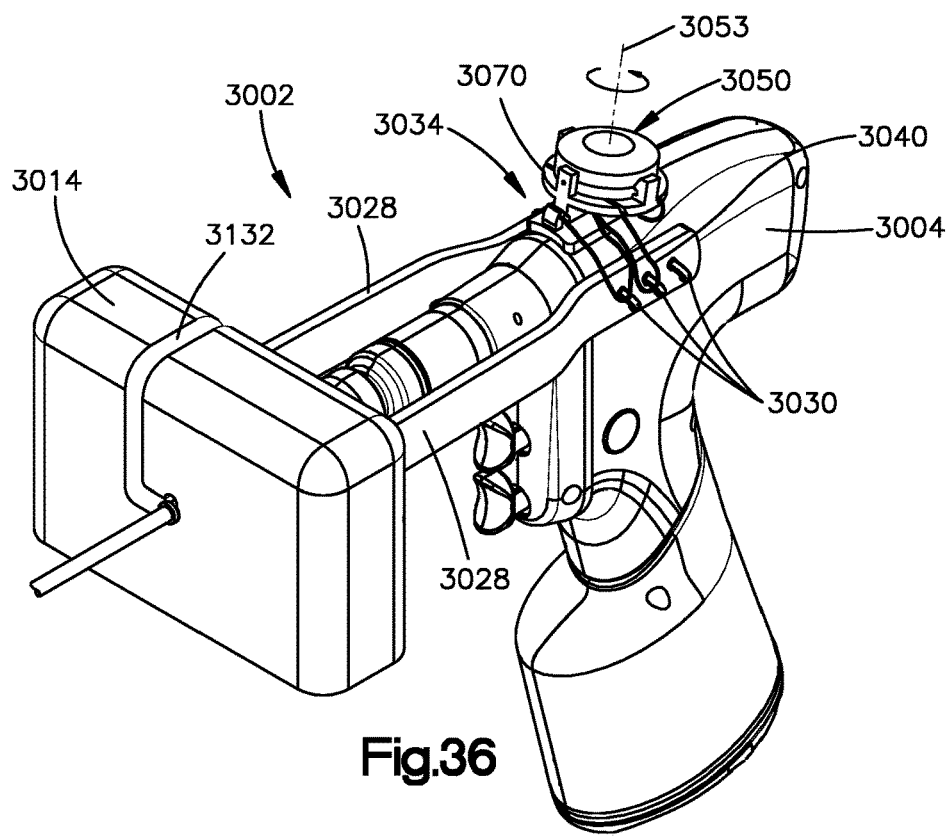
FIG. 36 is a perspective view of a distal targeting device employing a tether to couple the device to a power tool, with the tether is shown loosely attached, according to another embodiment of the present disclosure.
Figure 37:
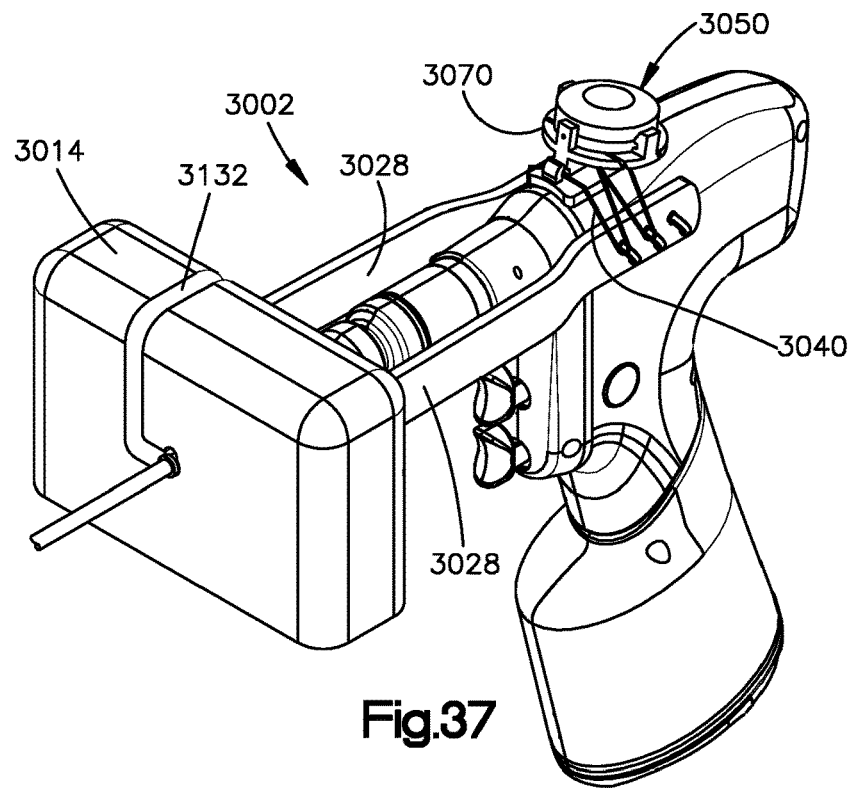
FIG. 37 is a perspective view of the distal targeting device of FIG. 36, showing the tether tightened.

Referring now to FIG. 36 through 39, another embodiment of a distal targeting device 3002 is shown. As shown in FIG. 36, the distal targeting device 3002 can include a bridge 3020 having branches 3028 that are coupled to a field generator 3014. The field generator 3014 has a transverse-entry opening 3132 for receiving a shaft of a power tool 3004 coupled to the distal targeting device 3002. The shaft seat can be located substantially at the geometric center of the field generator 3014. In the present embodiment, the branches 3028 are bracketed against opposite lateral sides of the power tool 3004 by an attachment device 3034 of the bridge 3020. The attachment device 3034 can include a tether 3040. The branches 3028 can include couplers, such as cleats 3030, extending laterally outward from the branches 3028, such as at proximal portions of the branches 3028. The tether 3040 is configured to be coupled to the cleats 3030 so as to couple the branches 3028 to the attachment device 3024. FIG. 36 shows the tether 3040 loosely laced to the cleats 3030, while FIG. 37 shows the tether in a tightened configuration.

The attachment device 3034 comprising a mount 3070 that is configured to attach to a portion of the power tool, such as atop the motor cowling, for example. The mount 3070 can be configured to anchor the tether 3040. The tether 3040 can extend from a tensioning mechanism 3050. The tensioning mechanism 3050 can be releasably attachable to the mount 3070. The tensioning mechanism 3050 can include a dial 3052 rotatably coupled to a base 3054. The mount 3070 can define a mount surface 3055 for supporting the base 3054 of the tensioning mechanism 3050. The mount 3070 can also include a first coupling element, such as tabs 3060 configured to releasably couple to the base 3054 in a snap-fit manner, for example.

As shown in FIG. 36, the dial 3052 can define a rotation axis 3053. The dial 3052 can be coupled to an internal spool around which the tether 3040 is wound. The tensioning mechanism 3050 can be configured such that rotating the spool (via the dial 3052) relative to the base 3054 in a first rotational direction about the axis 3053 winds the tether 3040 further around the spool, which imparts tension to the tether 3040 and reduces the overall length at which the tether 3040 extends from the tensioning mechanism 3050. The tensioning mechanism 3050 can include a ratchet, whereby rotation of the spool and/or the dial 3052 in a second rotational direction opposite the first rotational direction is prevented when the ratchet is engaged. The ratchet can be engaged and disengaged by subsequent depressions of the dial 3052, for example.

Figure 38:
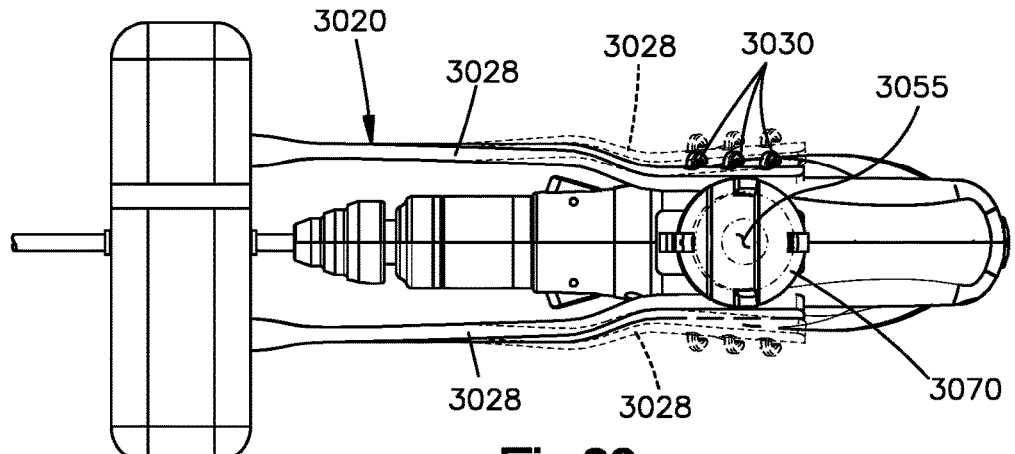
FIG. 38 is a top view of the distal targeting device of FIG. 36, with the tether and a tether tensioning mechanism removed for illustrative purposes.
Figure 39:
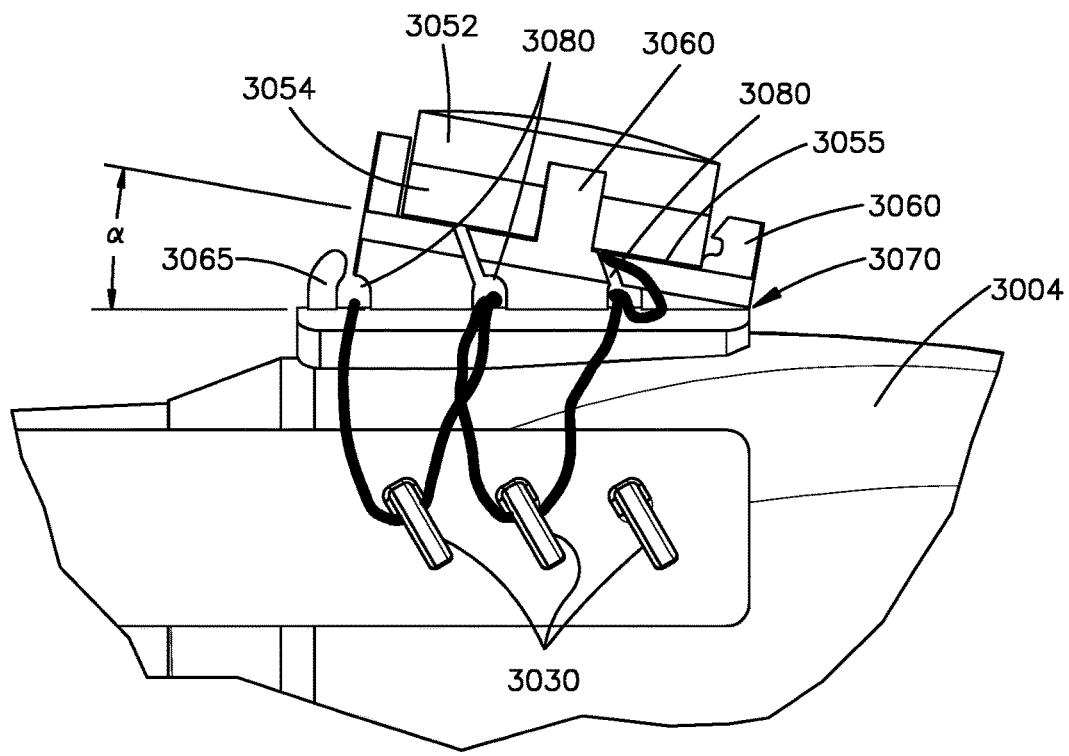
FIG. 39 is a partial side view of an attachment device of the distal targeting device of FIG. 36.

As shown in FIG. 39, the mount 3070 can define a second coupling element, such as anchoring slots 3080 recessed from the mount surface 3055, for example. A distal-most one of the anchoring slots 3080 can be at least partially defined by a front tab 3065. The anchoring slots 3080 can be configured to receive portions of the tether 3040. For example, the tether can be at withdrawn or at least slackened from the tensioning mechanism 3050 and wound through one or more, and optionally all, of the anchoring slots 3080 and around one or more, and optionally all, of the cleats 3030 in a manner anchoring the branches 3028 to the mount 3070. The tensioning mechanism 3050 can be coupled, via snap-fit, to the mount surface 3055 of the mount 3070 via the tabs 3060. The mount surface 3055 can be inclined distally at an acute angle α with respect to the shaft axis 18 (see FIG. 1) for enhanced access for the physician. The dial 3052 can then be rotated in the first rotational direction until the tether 3040 cinches the branches 3028 against the power tool 3004 in rigid fashion. As shown in FIG. 38, the branches 3028 of the present embodiment are laterally adjustable as needed, such as to fit power tools 3004 of different sizes and/or shapes. In the present embodiment, the branches 3028 themselves can be characterized as the clamp arms of the attachment device 3024.

Figure 40:
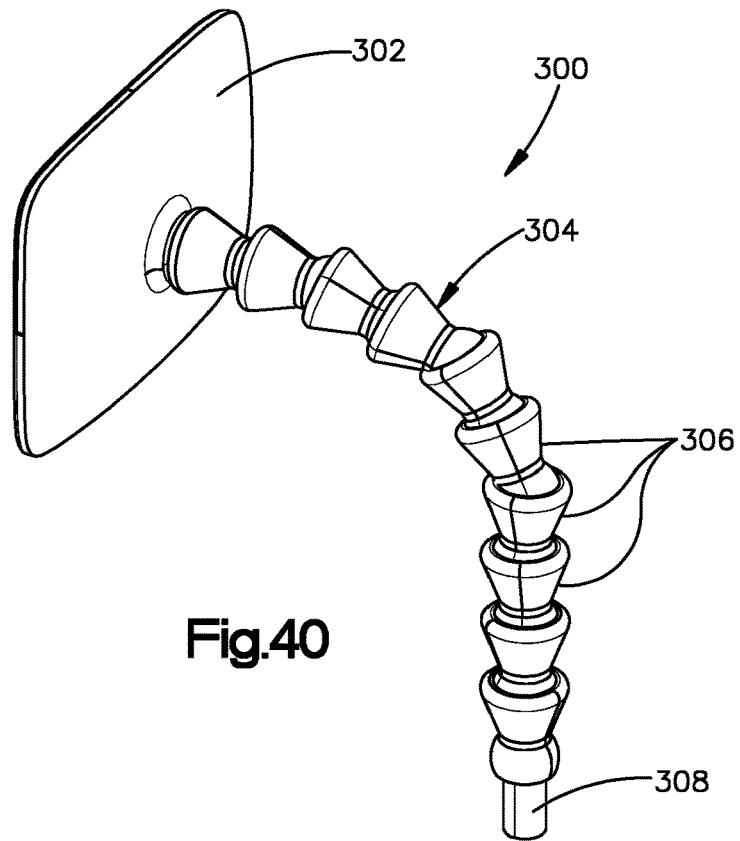
FIG. 40 is a rear perspective view of a display assembly for use with the distal targeting devices of the foregoing figures, according to an embodiment of the present disclosure.
Figure 41:
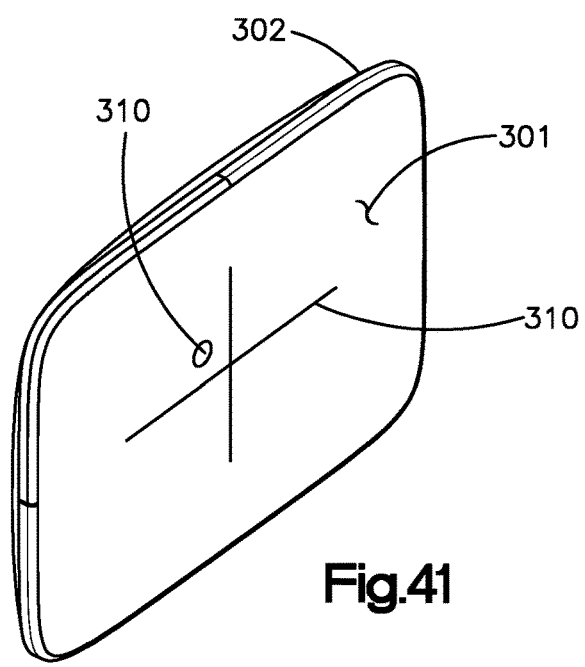
FIG. 41 is perspective view of a display screen of the display assembly of FIG. 40.
Figure 42:
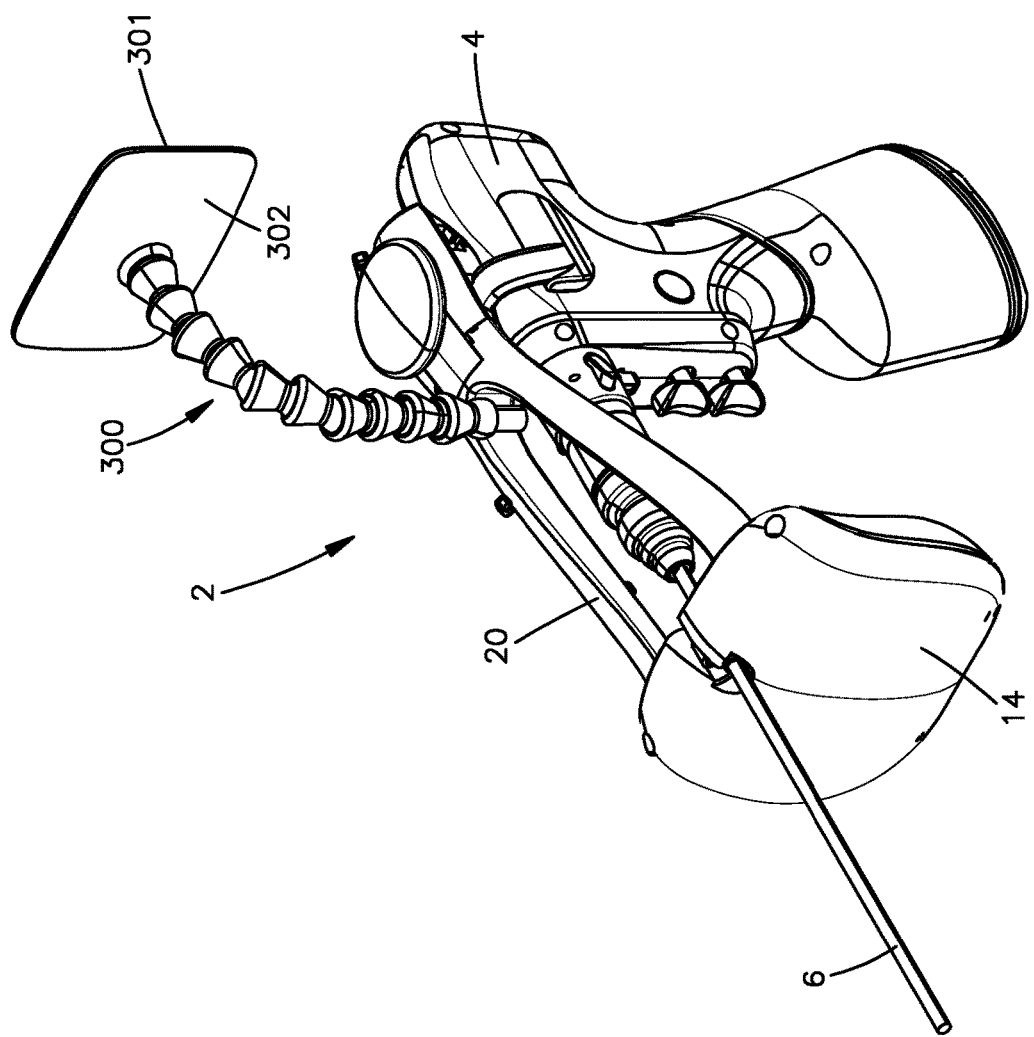
FIG. 42 is a perspective view of the display assembly of FIG. 40 coupled to the distal system device of FIG. 1.

Referring now to FIGS. 40 through 42, an example embodiment of a display assembly 300 for use with the distal targeting devices set forth above will now be described. As shown in FIG. 40, the display assembly 300 can include a display 302 coupled to an arm, such as an articulating arm 304, as shown. The articulating arm 304 can be formed of a plurality of articulable arm segments 306 coupled together. The arm 304 can also include an anchor segment 308 for connection to the distal targeting device. As shown in FIG. 41, the display 302 can include a view screen 301 providing visual indicia 310 of the relative positions of the distal end of the shaft 6 and the item being targeted by the distal targeting device, such as a locking screw of an intramedullary nail, by way of non-limiting example. As shown in FIG. 42, the display assembly 300 can be coupled to the bridge 20 of the distal targeting device 2. In other embodiments, the display assembly 300, or at least the display 302, can be coupled to the operating table, a bench, or another location within view of the physician during a distal targeting procedure.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A distal targeting device for a surgical instrument, comprising:
    a field generator having a coupling element configured to receive a shaft that is elongate along an axis; and
    a bridge connectable to the field generator so as to be spaced from the field generator in a proximal direction with respect to the axis, the bridge having an attachment device that is connectable to a tool that is configured to manipulate the shaft, the bridge having a pair of arms configured to clasp a body of the tool in a manner substantially rigidly coupling the bridge to the tool, wherein at least one of the arms is positionable with respect to the attachment member at a distance that is adjustable so as to enable the arms to substantially rigidly clasp tool bodies having one or more of various shapes and sizes.

2. The distal targeting device of claim 1, wherein at least one of the pair of arms defines a rack having teeth, and the attachment device comprises a pinion configured to engage the teeth of the rack such that rotation of the pinion causes the distance to increase or decrease.

3. The distal targeting device of claim 2, wherein the pinion is coupled to a knob configured to allow a physician to manipulate the pinion.

4. The distal targeting device of claim 3, wherein the knob defines ratchet teeth, and the attachment device comprises at least one pawl configured to engage the ratchet teeth, such that the at least one pawl is configured to 1) allow rotation of the pinion about a first rotational direction so as to decrease the distance, and 2) impede rotation of the pinion about a second rotational direction opposite the first rotational direction.

5. The distal targeting device of claim 1, wherein the attachment device comprises a tether engaged with a tensioning mechanism, the tether is configured to be attached to at least one of the arms, and the tensioning mechanism is configured to apply tension to the tether so as to reduce the distance.

6. The distal targeting device of claim 5, wherein each arm of the pair of arms defines one or more cleats, and the tether is configured to be laced around the one or more cleats of each of the arms to attach the tether to each of the arms, and the tensioning mechanism is configured to apply tension to the tether so as to reduce the distance.

7. The distal targeting device of claim 6, wherein the tensioning mechanism comprises a dial, and the tether is wound around a spool connected to the dial so that rotation of the dial applies the tension to the tether.

8. The distal targeting device of claim 1, wherein the attachment device comprises a translatable member that is translatable along a translation axis, the translatable member has a member contact surface, at least one arm of the pair of arms defines an arm contact surface in engagement with the member contact surface, and at least one of the member contact surface and the arm contact surface is oriented at an oblique angle with respect to the translation axis, such that translation of the translatable member in a first translation direction along the translation axis causes the at least one arm of the pair of arms to move so as to decrease the distance.

9. The distal targeting device of claim 8, wherein the translatable member defines ratchet teeth, and the attachment device includes at least one pawl in engagement with the ratchet teeth, the at least one pawl configured to 1) allow translation of the translatable member in the first translation direction and 2) inhibit translation of the translatable member in a second translation direction opposite the first translation direction.

10. The distal targeting device of claim 8, wherein the at least one arm of the pair of arms comprises a first arm portion configured to abut the body of the tool and a second arm portion defining the arm contact surface, and the at least one arm of the pair of arms pivotable about a pivot joint located between the first and second arm portions, such that reducing the distance causes the first arm portion to pivot against the body of the tool.

11. The distal targeting device of claim 1, wherein the at least one of the arms is connected to the attachment device by a spring hinge configured to bias the at least one of the arms against the body of the tool.

12. The distal targeting device of claim 11, wherein each arm of the pair of arms is connected to the attachment device by a respective spring hinge configured to bias the pair of arms against opposite sides of the body of the tool.

13. The distal targeting device of claim 12, wherein the bridge further comprises a second pair of arms configured to clasp the body of the tool in tandem with the pair of arms in a manner substantially rigidly coupling the bridge to the tool, each arm of the pair of arms and the second pair of arms is positionable with respect to the attachment member at a distance that is adjustable so as to enable the arms to substantially rigidly clasp tool bodies having one or more of various shapes and sizes, and each arm of the second pair of arms is connected to the attachment device by a respective spring hinge configured to bias the second pair of arms against the opposite sides of the body of the tool.

14. A field generator configured to align a shaft of a surgical instrument with a target, comprising:
a housing containing field generator circuitry and;
a coupling element at least partially defining an opening, the opening having an opening proximal end and an opening distal end spaced from one another along a longitudinal direction, the opening being open in a transverse direction that is substantially perpendicular to the longitudinal direction so as to receive the shaft without a distal end or a proximal end of the shaft passing through the opening.

15. The field generator of claim 14, wherein the opening is a slot having a first slot portion in communication with a second slot portion, the first slot portion being open in the transverse direction, the second slot portion defining an internal end of the opening, and the second slot portion is spaced from the first slot portion.

16. The field generator of claim 14, further comprising a shaft mount that is movably disposed within the housing, wherein the shaft mount is configured to move between a first position and a second position, such that 1) in the first position, the shaft mount retains the shaft within the opening, and 2) in the second position, the shaft is unrestrained by the shaft mount.

17. The field generator of claim 16, wherein at least one of the opening and the shaft mount comprises a bearing surface for rotationally bearing the shaft.

18. The field generator of claim 14, wherein the coupling element defines a shaft seat in communication with the opening.

19. The field generator of claim 18, wherein the shaft seat is located substantially at a geometric center of the field generator circuitry or is vertically offset from the geometric center of the field generator circuitry.

20. A distal targeting system, comprising:
a power tool having a tool body and a receiving element;
a shaft elongated along an axis extending along a longitudinal direction, a proximal portion of the shaft receivable in the receiving element;
a field generator having a coupling element configured to receive the shaft; and
a bridge connectable to the field generator so as to be spaced from the field generator in a proximal direction with respect to the axis, the bridge having an attachment device that is connectable to the power tool, wherein the bridge includes a pair of arms configured to clasp the tool body in a manner substantially rigidly coupling the bridge to the power tool, wherein at least one of the arms is positionable with respect to the attachment device at a distance that is adjustable so as to enable the arms to 1) substantially rigidly clasp the tool body, 2) release the tool body, and 3) substantially rigidly clasp a second tool body having one or more of a different size and shape than the tool body.

21. The distal targeting system of claim 20, wherein the attachment device comprises an actuator configured to reposition the at least one arm so as to adjust the distance.

22. The distal targeting system of claim 20, wherein the field generator further comprises a linkage, the bridge further comprises one or more couplers located at a distal end of the bridge, and the linkage is releasably connectable to the one or more couplers of the bridge.

* * * * *